(12) United States Patent
Khowaylo et al.

(10) Patent No.: US 10,272,177 B2
(45) Date of Patent: Apr. 30, 2019

(54) JOINT REPLACEMENT OR JOINT RESURFACING DEVICES, SYSTEMS AND METHODS

(71) Applicant: Acuitive Technologies, Inc., Allendale, NJ (US)

(72) Inventors: Alex Khowaylo, Upper Saddle River, NJ (US); James Malayter, Centre Hall, PA (US); Michael P. McCarthy, Ho-Ho-Kus, NJ (US); David Washburn, Ringwood, NJ (US)

(73) Assignee: Acuitive Technologies, Inc., Allendale, NJ (US)

( * ) Notice: Subject to any disclaimer, the term of this patent is extended or adjusted under 35 U.S.C. 154(b) by 1 day.

(21) Appl. No.: 15/638,930

(22) Filed: Jun. 30, 2017

(65) Prior Publication Data

US 2017/0296699 A1 Oct. 19, 2017

Related U.S. Application Data

(62) Division of application No. 14/737,697, filed on Jun. 12, 2015, now Pat. No. 9,713,655.

(Continued)

(51) Int. Cl.
*A61F 2/38* (2006.01)
*A61L 27/30* (2006.01)
(Continued)

(52) U.S. Cl.
CPC .......... *A61L 27/306* (2013.01); *A61L 27/045* (2013.01); *A61L 27/06* (2013.01); *A61L 27/56* (2013.01);
(Continued)

(58) Field of Classification Search
CPC ...... A61F 2/34; A61F 2/36; A61F 2/38; A61F 2002/30107
See application file for complete search history.

(56) References Cited

U.S. PATENT DOCUMENTS 5,037,438 A 8/1991 Davidson
5,356,436 A 10/1994 Nonami
(Continued)

FOREIGN PATENT DOCUMENTS

CA 2451612 1/2003
EM 803234 10/1997
(Continued)

OTHER PUBLICATIONS

Ni. G.X. et al., "Nano-mechanics of bone and bioactive bone cement interfaces in a load-bearing model," Biomaterials, 27(9), (2006), pp. 1963-1970.
(Continued)

*Primary Examiner* — Jason-Dennis N Stewart
(74) *Attorney, Agent, or Firm* — McCarter & English, LLP

(57) ABSTRACT

Joint resurfacing and/or replacement devices, systems and methods that include thin film ternary ceramic coatings that are effective to provide reliable articulation and bearing surfaces and protection of both articular and modular junction surfaces from the potential for corrosion, wear, and fretting, and reduce the potential for release of metal ions from the joint systems. Isoelasticity is provided according to the particular joint resurfacing/replacement devices, systems and methods based on parameters that include material of construction, porosity and coating system. The thin film ternary ceramic coatings may be functionalized to enhance hydrophilicity and may be employed in any anatomical articulating joint region. Titanium alloy composite structures are provided that include an ultra-porous structured titanium (Continued)

alloy bone fixation surface and an opposed solid articular surface and a thin film ternary ceramic coating applied to one or both opposed surfaces.

15 Claims, 15 Drawing Sheets

Related U.S. Application Data

(60) Provisional application No. 62/087,483, filed on Dec. 4, 2014, provisional application No. 62/042,030, filed on Aug. 26, 2014, provisional application No. 62/011,773, filed on Jun. 13, 2014.

(51) Int. Cl.
*A61L 27/04* (2006.01)
*A61L 27/06* (2006.01)
*A61L 27/56* (2006.01)
*A61F 2/30* (2006.01)

(52) U.S. Cl.
CPC . *A61F 2002/30107* (2013.01); *A61L 2400/18* (2013.01); *A61L 2430/02* (2013.01); *A61L 2430/24* (2013.01)

(56) References Cited

U.S. PATENT DOCUMENTS

| | | | |
|---|---|---|---|
| 6,087,553 A | 7/2000 | Cohen et al. | |
| 6,682,567 B1 | 1/2004 | Schroeder | |
| 6,723,674 B2 | 4/2004 | Wang et al. | |
| 7,074,223 B2 | 7/2006 | Axen et al. | |
| 7,968,209 B2 | 6/2011 | Pawar et al. | |
| 8,007,854 B2 | 8/2011 | Wei et al. | |
| 8,067,069 B2 | 11/2011 | Li | |
| 8,257,835 B2 | 9/2012 | Jani et al. | |
| 8,309,161 B2 | 11/2012 | Overholser et al. | |
| 9,011,965 B2 | 4/2015 | Gan et al. | |
| 9,051,639 B2 | 6/2015 | McEntire et al. | |
| 9,333,083 B2 | 5/2016 | Li et al. | |
| 9,457,126 B2 | 10/2016 | Pawar et al. | |
| 9,713,655 B2 | 7/2017 | Khowaylo et al. | |
| 2005/0164041 A1 | 6/2005 | Dunsmore et al. | |
| 2006/0184251 A1 | 8/2006 | Zhang et al. | |
| 2007/0173952 A1 | 7/2007 | Hermansson et al. | |
| 2008/0262626 A1 | 10/2008 | Raugel | |
| 2010/0035051 A1 | 2/2010 | Yilbas et al. | |
| 2010/0312352 A1 | 12/2010 | Antolotti et al. | |
| 2011/0066253 A1 | 3/2011 | Langhorn et al. | |
| 2011/0270404 A1 | 11/2011 | Khan et al. | |
| 2012/0136454 A1 | 5/2012 | Ely et al. | |
| 2013/0226307 A1 | 8/2013 | McEntire | |
| 2013/0345793 A1 | 12/2013 | Pacetti | |
| 2014/0316532 A1 | 10/2014 | Bigsby et al. | |
| 2014/0324184 A1 | 10/2014 | Bigsby et al. | |
| 2015/0005887 A1 | 1/2015 | Dimitrakopoulos | |

FOREIGN PATENT DOCUMENTS

| | | |
|---|---|---|
| EP | 0597553 | 5/1994 |
| EP | 1290992 | 3/2003 |
| EP | 1433443 | 6/2004 |
| EP | 1679088 | 12/2007 |
| EP | 1923079 | 7/2011 |
| GB | 2397765 | 8/2004 |
| KR | 1336408 | 12/2013 |
| SI | 23312 | 9/2011 |
| WO | WO 2005/070344 | 8/2005 |

OTHER PUBLICATIONS

Hamelynek, K. J. et al., "Ceramic Surface Engineered Metal-on-Metal Hips System for Total Hip Arthroplasty and Resurfacing Hip Arthroplasty," ACCIS, 2009.
Murr, L.E. et al., "Next Generation Orthopaedic Implants by Additive Manufacturing Using Electron Beam Melting," International Journal of Biomaterials, vol. 2012 (2012), Article ID 245727.
Liao, W.F. et al., "Preparation and properties of plasma sprayed strontium-doped calcium polyphosphate coating for bone tissue engineering," Ceramics International 40(1), (2014), pp. 805-809.
Smith&Nephew, Birmingham Hip Resurfacing, www.Rediscoveryourgo.com/bhrbirminghamhipresurfacing.aspx, visited May 7, 2014.
Wikipedia, "Ceramic," http://en.wikipedia.org/wiki/Ceramic, visited May 7, 2014.
Implantcast, "The use of Ceramic Coatings in Orthopaedic Implants," www.implantcast.de.
PCT International Search Report and Written Opinion for PCT International Application No. PCT/US2015/035481 dated Sep. 18, 2015.
U.S. Appl. No. 14/737,697, filed Jun. 12, 2015, U.S. Pat. No. 9,713,655.
U.S. Appl. No. 62/087,483, filed Dec. 4, 2014.
U.S. Appl. No. 62/042,030, filed Aug. 26, 2014.
U.S. Appl. No. 62/011,773, filed Jun. 13, 2014.

Cervical Artificial Disc Replacement

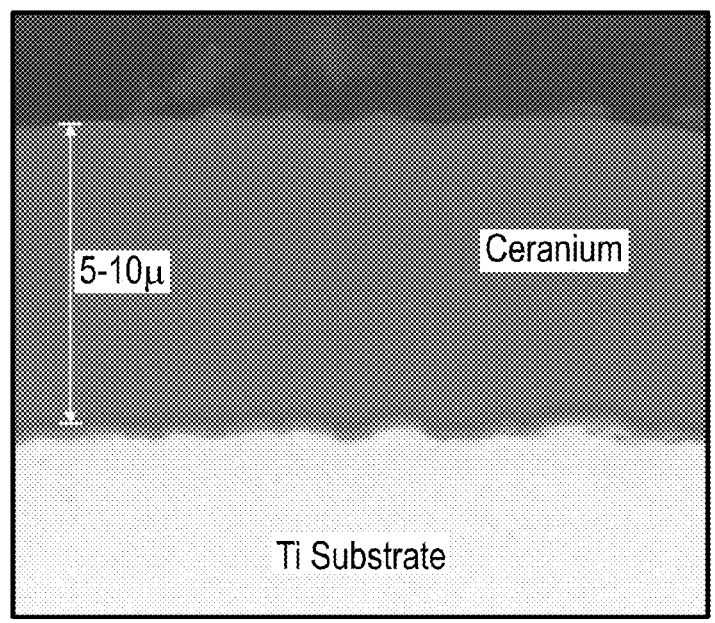
FIG. 10
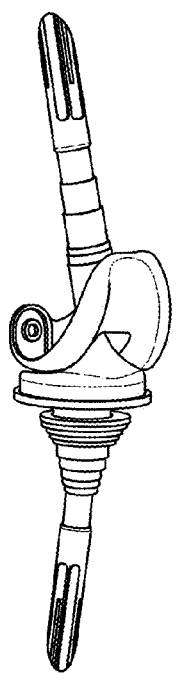
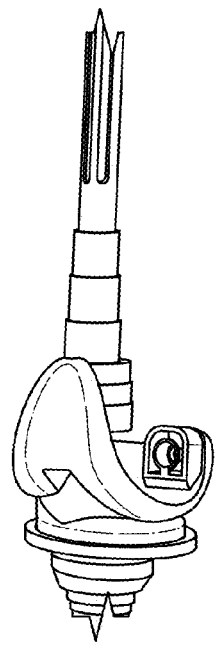
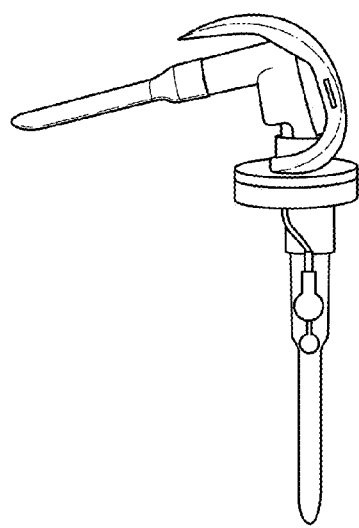
FIG. 11A     FIG. 11B     FIG. 11C

JOINT REPLACEMENT OR JOINT RESURFACING DEVICES, SYSTEMS AND METHODS

CROSS-REFERENCE TO RELATED APPLICATIONS

The present application is a divisional patent application that claims priority benefit to a non-provisional application entitled "Joint Replacement or Joint Resurfacing Devices, Systems and Methods," which was filed on Jun. 12, 2015, and assigned Ser. No. 14/737,697, and which claimed priority benefit to three (3) provisional applications, as follows: (i) a provisional patent application entitled "Modular Length Hip Resurfacing and Replacement Device," which was filed on Jun. 13, 2014 and assigned Ser. No. 62/011,773; (ii) a provisional patent application entitled "Isoelastic Joint Replacement Device," which was filed on Aug. 26, 2014 and assigned Ser. No. 62/042,030; and (iii) a provisional patent application entitled "Modular Joint Resurfacing and Replacement Devices," which was filed on Dec. 4, 2014 and assigned Ser. No. 62/087,483. The entire contents of the foregoing non-provisional patent application and each of the foregoing provisional patent applications are incorporated herein by reference.

BACKGROUND

1. Field of the Disclosure

The present disclosure relates to orthopedic joint resurfacing and/or replacement devices and systems. The present disclosure also relates to constructs, designs, materials and methods of use and manufacture of articulating devices, as well as protection of metallic junctions and fittings thereof. More specifically, the present disclosure advantageously addresses distinct aspects of orthopedic joint replacement and/or resurfacing systems and methodologies that are applicable to all joint and spinal disc locations in the body, and that in exemplary implementations effectively enhance overall efficacy and performance by combined implementation and/or utilization of (i) an integral titanium alloy composite structure having two sides—on one side an ultra-porous structured titanium alloy bone fixation surface and on the opposing side an integral solid articular surface—wherein the composite structure may be advantageously fabricated using an additive manufacturing process, (ii) an overall device design that delivers advantageous isoelasticity to bone, (iii) a thin film ternary ceramic coating applied to one or both opposed surfaces of a replacement or resurfaced device/system, and (iv) coating functionalization of one or both implant surfaces to increase hydrophilicity to (1) improve articular wear on one side, and (2) to promote osteoblast activity on the bone fixation side.

Additional features, functions and applications of the disclosed devices, systems and methods will be apparent from the description that follows.

2. Related Background Art

Natural joint articulation is stable and virtually wear-free due to the biological, mechanical, and tribological anatomy. However, when replacing natural articulation (e.g., due to deformity, degeneration, trauma, disease, etc.) through total joint replacement or joint resurfacing, synthetic materials are substituted in whole or in part for the anatomic living cartilage and physiologic geometries. It has been challenging for synthetic materials (e.g., metal, ceramic and polyethylene materials, etc.) to perform well under joint loading conditions within the biologic environment of the human body. In order for the joint articulation surfaces to be replaced by synthetic materials and designs, other factors must be considered, specifically those of fixation of the synthetic articulation to host bone, and the protection of any modular fittings or junctions that comprise the joint replacement of resurfacing implants.

In view of these considerations, there are at least three materials/design factors that require increased attention: i) the articulating interfaces of the joint replacement; ii) modular fittings, junctions, or couplings that make up the construction of the implant, and iii) the bone fixation surface of the implant that allows for durable stability of the implant in host bone.

Regarding the articulating interfaces of the implant, wear of the articulation surfaces can be problematic, and debris from such wear has caused bone lysis and tissue toxicity in some designs and materials. This wear can be accelerated through the introduction of third body particles that are generated at the articulating interface and elsewhere, and by surface scratches.

Regarding modular fittings and junctions, wear and fretting of modular fittings has been shown to be increasingly problematic and has resulted in galvanic, crevice and/or fretting corrosion of these implant surfaces. Patients receiving implanted joint or spinal replacement devices undergo millions of gait cycles during the course of their implant lifespan, where even minor relative, but unintended, motion could be a source for metal-metal wear, which could result in the release of wear debris particles and metal ions into the host tissues and/or into undesirable articulation between metal-on-metal components and/or metal-on-polyethylene components and associated wear. There is a danger, particularly for younger and/or active patients, of eventual wear and/or subsequent loosening of the device from host bone due to a biologic reaction to wear debris. Wear particles present in the abutting articulation region have been shown in particular to accelerate ultrahigh molecular weight polyethylene (UHMWPE) wear, carrying with it potential consequences of particulate-generated bone lysis and component failure that may result in ultimate failure of the joint replacement itself.

In addition, particulate debris generation could occur with backside wear associated with modular couplings and/or components (e.g., acetabular cups, tibial trays, etc.). For example, modular acetabular cups may include a separate polyethylene, e.g., a polyethylene liner snapped into a metal cup, which can produce micro-motion therebetween (e.g., polyethylene abrasion against a metal inner diameter wall), releasing debris particles that can induce bone lysis.

Further, there exists a known galvanic reaction between any two dissimilar metals, or metallic interfaces intended to be locked but that undergo relative motion, especially in the presence of a conductive medium, such as body fluid, that may lead to galvanic corrosion and/or release of metal particles and metal ions into host tissue. Certain metal ions are generally toxic to tissue.

Regarding the bone fixation interface, implant fixation to bone has been challenged by increased patient activity, the presentation of younger patients for arthroplasty, and by stress shielding. Stress shielding is generally caused when the implant construct is considerably stiffer than its supporting bone, bypassing the bone of necessary stress and causing its resorption, de-mineralization, and loss of strength. Bone of lesser density is more susceptible to microfracture and/or invasion by wear debris, which may accelerate the lysis and loosening cycle.

Also regarding implant fixation and biocompatibility of the bone fixation interface, release of metal ions can have an untoward effect. Oxidation of both the debris and freshly exposed metal surfaces associated with joint repair/replacement reduces oxygen and pH levels of the trapped body fluids. This phenomenon may accelerate breakdown of the metal surface passivation layer by creating conditions that increase the solubility of the metal oxide film associated with a metal implant. Additionally, oxidized debris is typically harder than the surfaces from which it came and acts as an abrasive third body agent that can increase the rate of fretting. Indeed, the processes may feed off each other.

An additional goal in orthopedic joint replacement or resurfacing procedures is to mitigate third body particulate debris that can develop due to the breakdown of bone cement. Therefore, joint replacement using a cementless fixation device has become a common and desired procedure for addressing osteoarthritis (arthrosis) in patients afflicted with the condition. The cementless fixation procedure may involve the use of a stiff solid metal device with surfaces intended for biologic fixation of the device to bone. Many metal devices are generally stiffer than the bone to which they are affixed by the nature of their design. This mismatch in stiffness can result in the biologic loss of bone density surrounding and supporting the solid metal device (e.g., by stress shielding), which can result in the eventual loosening of the device from the host bone.

As is apparent, there is a need in all forms of orthopedic (i) articulation, (ii) modular junction couplings and interfaces, and (iii) implant fixation, to eliminate and/or reduce generation of wear and wear debris, to increase surface wettability and lubricity for wear reduction, reduce the potential for fretting and corrosion, to reduce/eliminate the occurrence of stress shielding, and to increase overall durability of the orthopedic device fixation through maintained host bone support, as well as to protect those surfaces from metal particle and ion release.

In addition, in view of the challenges outlined above, there is a need for orthopedic joint replacement and/or joint resurfacing devices, systems and methods that are fabricated to protect modular interfaces from direct metal-metal contact, particulate debris, fretting, wear, galvanic corrosion, and crevice corrosion, in whole or in part. There is also a need for orthopedic joint replacement and/or joint resurfacing devices, systems and methods that include articulation surfaces and/or substrates that effectively load supporting bone from a physiologic standpoint, thereby avoiding loss of bone density through stress shielding. Indeed, there is a need for joint replacement and/or joint resurfacing devices, systems and methods that deliver isoelastic functionality that closely replicates the stiffness of the host bone to maintain healthy bone density and fixation of the device within the patient and that is biocompatible, meaning that host bone has an affinity to the fixation surface of the implant.

These and other needs are satisfied by the orthopedic joint replacement and joint resurfacing devices, systems and methods disclosed herein, including specifically the advantageous coating materials and coating systems disclosed herein for use in orthopedic joint replacement and joint resurfacing modalities.

SUMMARY

The present disclosure provides advantageous orthopedic joint resurfacing and replacement devices, systems and methods that enhance overall efficacy and performance across all joint locations in the body, including specifically (i) an integral titanium alloy composite structure having two sides—on one side an ultra-porous structured titanium alloy bone fixation surface and on the opposing side an integral solid articular surface—wherein the composite structure may be advantageously fabricated using an additive manufacturing process, (ii) an overall device design that delivers advantageous isoelasticity to bone, (iii) a thin film ternary ceramic coating applied to one or both opposed surfaces of a replacement or resurfaced device/system, and (iv) coating functionalization of one or both implant surfaces to increase hydrophilicity to (1) improve articular wear on one side, and (2) to promote osteoblast activity on the bone fixation side.

The disclosed joint replacement and/or joint resurfacing devices, systems and methods may be used in all anatomical regions, including specifically articulating joints and joint regions, e.g., hip, knee, ankle, shoulder, elbow, spine, etc.

In one aspect, the disclosed joint replacement and/or joint resurfacing devices and systems may include materials specifically suited to coat articular surfaces to reduce friction, improve hardness to resist scratching, and increase lubricity to virtually eliminate wear.

In another aspect, the disclosed joint replacement and/or joint resurfacing devices and systems may include materials specifically suited to protect modular junctions and articulating interfaces from direct metal-metal contact, wear, fretting, galvanic corrosion and crevice corrosion.

In still another aspect, the disclosed joint replacement and/or joint resurfacing devices and systems may include materials specifically suited to seal off metal interfaces from ion release while improving biological affinity through functionalization thereof, hence improving biological fixation of the implant.

In an additional aspect, the disclosed joint replacement and/or joint resurfacing devices and systems may be designed and fabricated from materials whereby the implants exhibit isoelasticity relative to the host bone. As such, the bone is more physiologically loaded and either maintains or regains its density, enabling better and longer lasting support of the implant in vivo.

According to exemplary implementations of the present disclosure, thin film ternary ceramic coatings and coating systems are disclosed for use in orthopedic joint replacement and joint resurfacing applications. The disclosed thin film ternary ceramic coatings are biologically, chemically, and mechanically compatible (e.g., chemically and biologically inert under physiologic conditions) with the modular components to which they are applied (e.g., skeletal, muscular, medical implant components, etc.). The disclosed thin film ternary ceramic coatings may be applied to metal joint replacement components by chemical or physical vapor deposition, cathodic arc deposition, magnetron sputtering and/or any other suitable technique.

Exemplary thin film ternary ceramics for use according to the present disclosure may include, inter alia, titanium aluminum nitride (TiAlN), titanium carbon nitride (TiCN), titanium niobium nitride (TiNbN), titanium silicon nitride (TiSiN), titanium zirconium nitride (TiZrN), titanium chromium nitride (TiCrN), and the like. The disclosed coating systems may also include alternative materials that exhibit desirable properties, such as metal nitride, metal carbide, metal oxide, diamond-like carbon (DLC) and/or combinations thereof.

The disclosed thin film coating materials and systems are effective in maintaining an ability to fit and lock joint-related components together with integrity. In addition, the disclosed thin film coating materials/systems are tough and durable, thereby advantageously resisting wear, scratching, corrosion (e.g., galvanic corrosion, crevice corrosion, etc.), and fretting. The disclosed thin film coating materials/systems further function to prevent penetration by metallic ions or body fluids, thereby substantially sealing off the metal of fitted components from each other, providing a barrier to the release or transmission of metallic ions, and otherwise maintaining the integrity of the metallic environment.

For example, titanium alloy components may be coated, hardened and/or sealed using the thin film coatings disclosed herein to increase surface hardness, reduce friction, obviate wear, and/or provide a barrier from particle and ion release. In exemplary applications of the disclosed coating materials/systems, the thin film coating is applied at a thickness of less than 20 microns.

The disclosed thin film ternary ceramic coating further function to enable the disclosed joint replacement and/or joint resurfacing designs, systems and methods to load host bone in a physiologically effective manner, thereby avoiding loss of bone density through stress shielding. Thus, in exemplary implementations, the disclosed joint replacement and/or joint resurfacing devices, systems and methods deliver isoelastic functionality that closely replicates underlying natural bone.

Of note, orthopedic joint replacement and resurfacing implants are often comprised of two main components on either side of the joint. The two components are generally in contact with each other through opposed, articulating surfaces (there are exceptions where a component is used on one side of the joint to articulate against native cartilage, e.g. hemiarthroplasty). Each component of the joint replacement, therefore, generally entails two sides, a fixation surface and an articulating surface. According to the present disclosure, an isoelastic joint replacement device (i.e., a joint replacement device that is isoelastic relative to host bone) may include a solid metal or metal alloy substrate having an articulating first side and a fixation second side, a hardened articulating thin film coating on the first side of the solid metal or metal alloy substrate, and a porous structure attached or associated with the second side of the solid metal/metal alloy substrate The porous structure may vary in porosity and density throughout at least a portion thereof, or may exhibit consistent (or relatively consistent) porosity throughout the porous structural region.

In exemplary implementations of the present disclosure, a titanium alloy substrate is formed, e.g., by an additive manufacturing process, with desired porosity characteristics to provide/support desired bone in-growth functionalities. Exemplary additive manufacturing process information is provided, for example, by L. E. Murr et al. in "Next Generation Orthopaedic Implants by Additive Manufacturing Using Electron Beam Melting," International Journal of Biomaterials, Volume 2012 (2012), Article ID 245727, the contents of which are incorporated herein by reference. The porosity may be uniform or variable. The use of titanium alloy is desirable as compared, for example, to a cobalt chrome substrate, because the titanium alloy substrate more closely matches the properties of bone to which the substrate will be mounted/joined. The titanium alloy substrate may include physical feature(s) to enhance localized strength/rigidity, e.g., ribbing, particularly in instances where the porosity and/or dimensions of the substrate may require such strengthening.

The disclosed titanium alloy articulating surface substrate is non-porous and is advantageously coated with a thin film ternary ceramic coating to provide a desired level of wear and scratch resistance, increased hardness, and friction reduction. Hence, through the use of the disclosed thin film ternary ceramic coating, the thickness of the component can be limited, preserving bone stock that would otherwise require removal, e.g., to accommodate a thicker (e.g. polyethylene) liner/insert sub-component. The titanium alloy component—which is of reduced size/thickness—is increasingly flexible as its section is thinned in design, to the point of being isoelastic to bone. The overall design objective, i.e., isoelastic component that nonetheless provides desired wear and scratch resistance, hardness, and friction reduction, is advantageously achieved by applying a thin film ternary ceramic coating to the articulation surface of the titanium alloy component. Of note, the porous region of the titanium alloy component—which provides fixation functionality relative to host bone—also advantageously receives a thin film ternary ceramic coating that enhances isoelasticity because, in part, of the close matching of modulus of the overall construct relative to underlying bone. Moreover, the thin film ternary ceramic coating acts as an inert barrier coating to protect the host tissue from liberation of particulate debris and metal ion transfer. Such inert surfaces have been shown to be biocompatible.

Functionalization of the coated articulating surfaces—e.g., through the addition of hydroxyl groups to the thin film ternary ceramic coating, thereby increasing wettability or hydrophilicity of the articulating surface—may be advantageously effected to achieve desired levels of lubricity and to reduce wear potential. Various means of functionalization may be effectuated according to the present disclosure, e.g., steam/pressure conditions in autoclave treatment, immersion in caustic potash, etc. Functionalization of the thin film ternary ceramic coating may thus be advantageously effected to achieve desired levels of hydrophilicity, which in turn yields improved or enhanced hydrophilicity that increases lubricity and improves articular wear properties. Functionalization of the bone fixation surfaces also advantageously helps to achieve desired levels of bone ingrowth and/or biologic fixation, which may be promoted/achieved according to the present disclosure. Thus, functionalization of the bone fixation region of an implant may improve the biologic environment to accommodate osteoblast proliferation and adhesion. In this way, desired levels of bone growth may be promoted and/or achieved according to the present disclosure.

In alternative implementations of the present disclosure, joint articulation components fabricated from one or more alternative materials (i.e., a material other than a titanium alloy) may be provided. In such alternative implementations, coating systems may be employed to achieve desired component properties.

Additional features, functions and benefits of the disclosed orthopedic joint replacement and joint resurfacing devices, systems and methods will be apparent from the detailed description which follows, particularly when read in conjunction with the accompanying figures.

BRIEF DESCRIPTION OF THE DRAWINGS

The foregoing features of the disclosure will be apparent from the following Detailed Description, taken in connection with the accompanying drawings, in which:

FIG. 10 is a sectional side view of a component with a thin film ternary ceramic coating on a titanium substrate; and FIGS. 11A to 11C are illustrative representations of modular knee stem extension devices and applications that may incorporate the teachings of the present disclosure.

DETAILED DESCRIPTION OF EXEMPLARY EMBODIMENT(S)

The present disclosure provides constructs, designs, materials, and methods of use and manufacture of orthopedic articulating devices (e.g., of orthopedic joint replacement or resurfacing devices), as well as protection of modular metallic junctions and fittings (e.g., taper fittings) thereof by obviating wear, fretting, corrosion (e.g., galvanic corrosion, crevice corrosion, inter-granular crevice corrosion, etc.), and/or particulate liberation between articulation members and modular couplings (e.g., tapered fitting) in total joint replacement and resurfacing devices (e.g., hip replacement device), such as due to relative motion, dissimilar metals, and the like. More specifically, the present disclosure relates to protection of articular joint surfaces, metallic modular junctions, joints and fittings, thereby supporting long term performance and load bearing with reduced risk of failure or complication due to a host of deleterious causes, as noted herein.

Figure 1A:
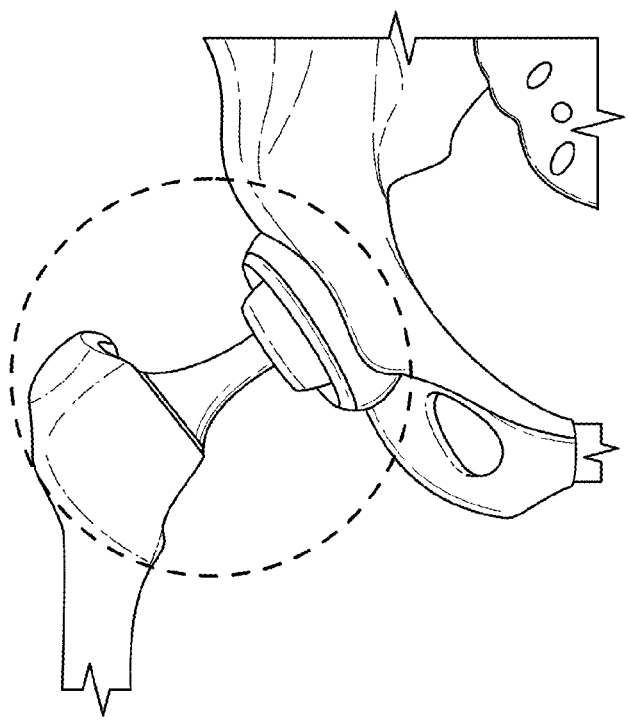
FIGS. 1A to 1G are illustrative representations of devices and applications that may incorporate the teachings of the present disclosure.
Figure 1B:
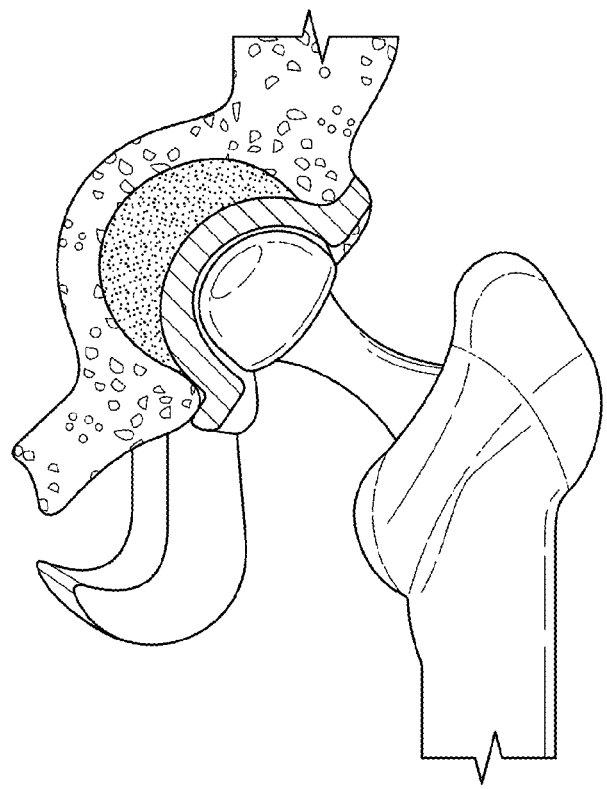

As noted above, the disclosed joint replacement and/or joint resurfacing devices, systems and methods may be used in all anatomical regions, including specifically articulating joints and joint regions, e.g., hip, knee, ankle, shoulder, elbow, spine, etc. FIGS. 1A-1G, FIGS. 2A-2H, FIGS. 3A-3F and FIGS. 11A-11C provide schematic views of a range of anatomical regions and orthopedic applications in which the present disclosure may be beneficially employed. As will be apparent to persons skilled in the art, the noted figures depict various orthopedic implants that feature one or more articular surfaces that may benefit from the disclosed coating systems and related design, material and fabrication parameters disclosed herein, including hip implants (FIGS. 1A-1B), knee/knee stem implants and extensions (FIGS. 1C-1E; FIGS. 12A-12C), ankle implants (FIG. 1F), hand and wrist implants (FIG. 1G, FIGS. 2A-2E), elbow implants (FIG. 2F), shoulder implants (FIGS. 2G-2H), and spinal/cervical implants (FIGS. 3A-3F).

As described herein, advantageous orthopedic joint resurfacing and replacement devices, systems and methods are disclosed that include (i) an integral titanium alloy composite structure having two sides—on one side an ultra-porous structured titanium alloy bone fixation surface and on the opposing side an integral solid articular surface—wherein the composite structure may be advantageously fabricated using an additive manufacturing process, (ii) an overall device design that delivers advantageous isoelasticity to bone, (iii) a thin film ternary ceramic coating applied to one or both opposed surfaces of a replacement or resurfaced device/system, and (iv) coating functionalization of one or both implant surfaces to increase hydrophilicity to (1) improve articular wear on one side, and (2) to promote osteoblast activity on the bone fixation side.

The detailed description which follows sets forth various implementations of the disclosed orthopedic joint resurfacing and replacement devices, systems and methods, including modular metallic junctions and fittings (e.g., taper fittings) thereof.

1. Modular Junction Protection:

Joint replacement procedures typically involve the use of solid metal devices (e.g., cobalt chromium alloy, titanium alloy, stainless steel, etc.) that are affixed to bone, but in many cases several metal sub-components are intended to be fitted together intraoperatively to form a component for one side of the joint. This combination of sub-components may facilitate adjustment of the size of the device to fit patient needs, such as is needed to accommodate varying femoral neck length and varying femoral head diameters in a hip prosthesis, or to add length to aspects of a particular component, such as the fixation stem of a tibial baseplate in knee replacement to augment fixation of that component.

Further, many sub-components use titanium alloy to facilitate bone ingrowth and material flexibility, and use cobalt chromium (CoCr) alloy as a bearing surface (e.g., against UHMWPE on an opposing articular surface). This combination of sub-components necessitates connecting dissimilar metals to each other. Placing two dissimilar materials in direct contact creates a risk of galvanic corrosion and/or metal ion leaching into the blood and/or surrounding tissue of the patient. To address these shortcomings—the disclosed thin film ternary ceramic coating may be applied to the titanium alloy and/or CoCr alloy, thereby preventing/eliminating galvanic, fretting and crevice corrosion. Thus, the present disclosure contemplates the application of a thin film ternary ceramic coating to a device (or device segment(s)), i.e., a substrate, which will be generally fixed or intraoperatively assembled to components fixed to the skeletal system to replace a joint (or a segment of a joint).

The disclosed thin film ternary ceramic coatings may be advantageously employed on modular junctions to form a non-porous layer of impermeable material on an underlying metal substrate to resist and/or prevent wear, ion leaching (e.g., particle liberation), galvanic reaction, and fretting, thereby prolonging the service life of the joint replacement implant and providing relief and functionality to a range of high demand patients. The disclosed thin film coatings (whose thickness is generally between 1 and 20 microns) are advantageously adapted to maintain the ability to fit and lock the modular components together with integrity, are tough and durable so as to resist wear, scratching, corrosion (e.g., galvanic corrosion, crevice corrosion, etc.), and fretting, and prevent penetration by metallic ions or body fluids (e.g., seal off the metal of the fitted components from each other, provide a barrier to the release or transmission of metallic ions, etc.). For example, titanium alloy components may be coated, hardened, and/or sealed with the disclosed thin film ternary ceramic coatings to increase surface hardness—obviate wear, and/or provide a barrier from particle and ion release.

In exemplary embodiments of the present disclosure, materials and methods for protecting metallic modular junctions and fittings designed into orthopedic joint replacement devices are thus provided. Exemplary protective coating materials include thin film ternary ceramics (TiAlN, TiNbN, TiCN, TiZrN, TiCrN, and others). Additional coating materials may also be employed, including carbides, oxides, diamond-like carbon (DLC), or mixes and combinations thereof. The disclosed coating materials are chemically and biologically inert under physiologic conditions, are hard and wear resistant, and serve as a tough and durable barrier to the release or transmission of metallic ions. The method of coating the underlying substrate (e.g., a metal joint replacement component) may include chemical or physical vapor deposition, cathodic arc deposition, magnetron sputtering, or other suitable coating technique.

The disclosed coatings may be advantageously applied at thicknesses of less than 20 microns so as to maintain the ability to fit and lock the modular components together with integrity, but to provide desirable levels of toughness and durability, thereby resisting or preventing wear, corrosion, fretting, and penetration by metallic ions or body fluids. The thin film coating may circumferentially and completely encase the modular interface of male and female taper geometries of a femoral head-trunnion assembly, or flat surfaces on knee replacement or other joint assembly.

In exemplary embodiments, the thin film ternary ceramic coating of less than 20 microns may be applied to the modular junction of a stem extension. The disclosed coating is generally non-permeable and firmly/securely attached or bonded to the metal junction or fitting section of each component, to harden the solid metal substrate for wear and scratch avoidance. The thin film, non-porous layer of impermeable material advantageously protects the underlying metal substrate and resists wear, ion leaching, fretting, galvanic, and crevice corrosion.

For example, the present disclosure may have application with respect to a joint replacement intramedullary stem extension for a knee replacement device (see FIGS. 12A-12C). The modular stem extension could assist in the stabilization and fixation of the knee replacement in the event of inadequate bony contact, bone loss, or sizing discrepancy. The modular junction of the stem extension may be advantageously coated with a thin film ternary ceramic (e.g., titanium aluminum nitride (TiAlN), titanium carbon nitride (TiCN), titanium niobium nitride (TiNbN), titanium silicon nitride (TiSiN), titanium zirconium nitride (TiZrN), titanium chromium nitride (TiCrN), and the like), diamond-like carbon, or metal nitride (e.g., titanium nitride), zirconia alumina, etc. that is non-permeable. The thickness of the thin film coating is generally less than 20 microns. The coating could be securely applied or attached to the metal junction or fitting section of each component. Thus, as is readily apparent, the disclosed systems and methods have wide-ranging applicability across all joint locations in the body.

2. Articular Surface Protection:

As noted above with reference to FIGS. 1A-1G, FIGS. 2A-2H and FIGS. 3A 3F, the present disclosure also relates to coatings of and coating systems for articulating components within a joint replacement or resurfacing device (e.g., medical device implants, metal or ceramic joint replacement components, etc.). The substrate surface and substrate roughness may be selected or adapted to facilitate effective adhesion of the coating thereto. The disclosed coatings are biologically, chemically, and mechanically compatible (e.g., chemically and biologically inert under physiologic conditions) with the components to which they are attached or applied (e.g., skeletal, muscular, medical implant components).

More specifically, application of the disclosed thin film coatings onto an articular surface is generally effective to reduce friction and avoid surface scratching, thereby avoiding wear. For example, the protection provided by the disclosed thin film ternary ceramic coatings makes it possible to employ titanium alloy as an articulating component substrate, notwithstanding that substrate components fabricated from titanium alloy would otherwise be undesirable due to tribological limitations associated with the titanium alloy materials. Also, since titanium alloy has been shown to be an advantageous bone ingrowth surface, a component can be manufactured, preferably using additive manufacturing, as a monolith, with a coated articulating surface first side and an ultraporous fixation second side. In clinical applications, it is possible to provide a first articulation side coated component in contact with a second, similarly coated component on the opposing side of the joint, and to experience effective, long term articulation without risk of failure or other deleterious effects. Furthermore, chemically functionalizing the thin film ternary ceramic to increase its hydrophilicity, in turn, increases lubricity, further reduces friction, and further limits wear potential.

Figure 1C:
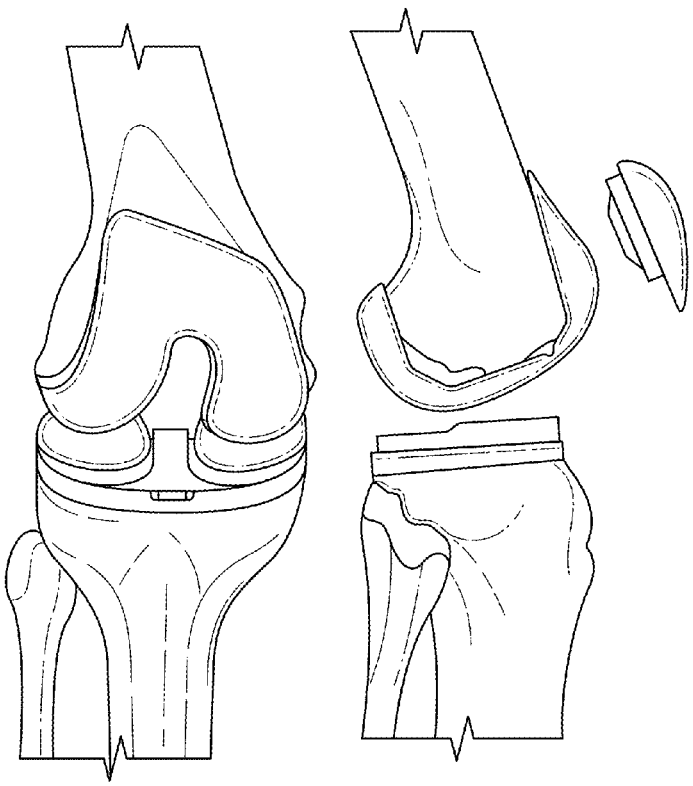
Figure 1D:
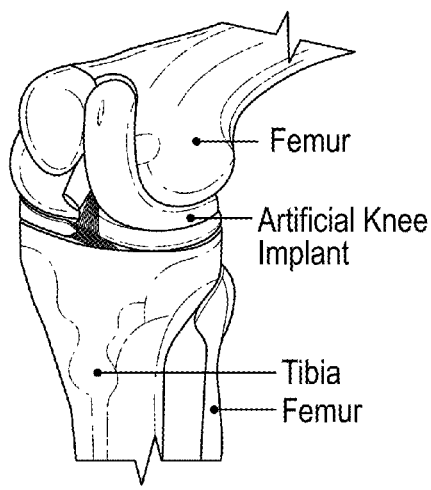
Figure 1E:
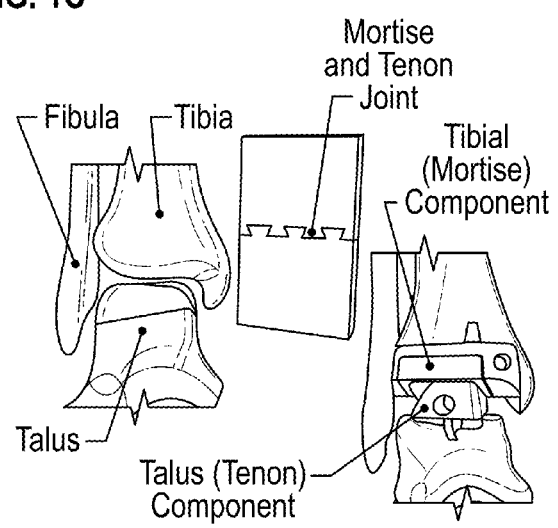
Figure 1F:
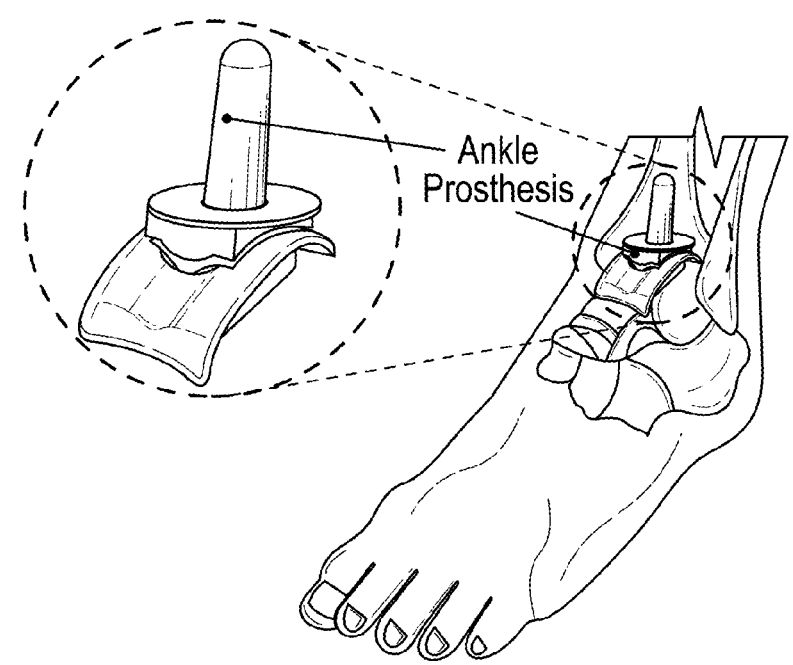
Figure 1G:
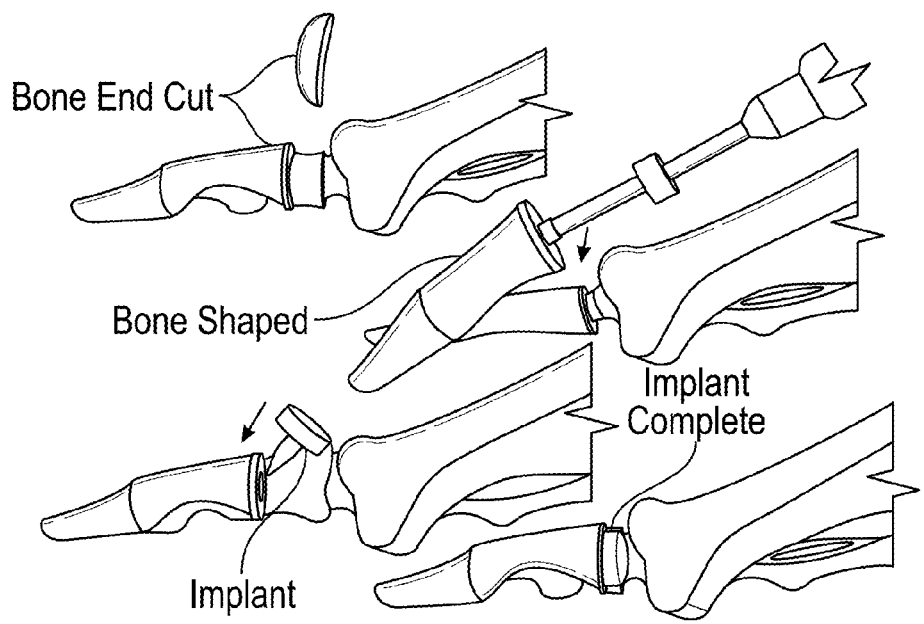
Figure 2A:
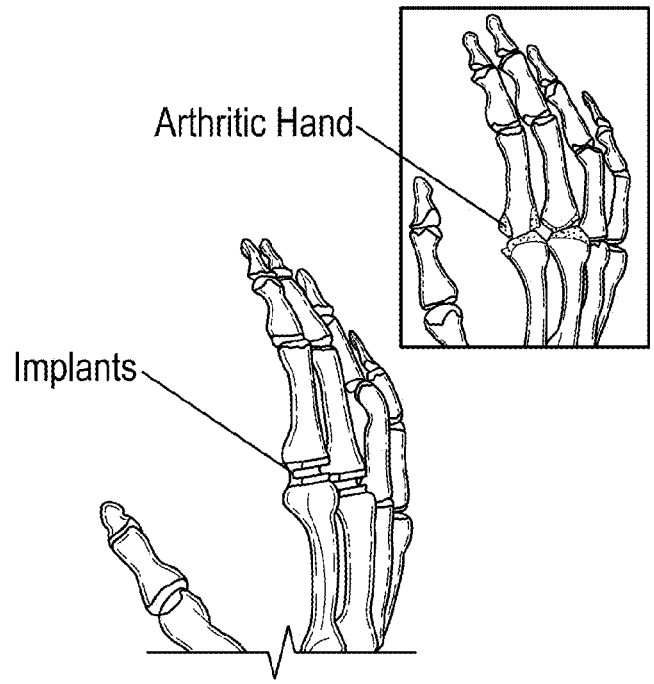
FIGS. 2A to 2H are illustrative representations of additional devices and applications that may incorporate the teachings of the present disclosure.
Figure 2B:
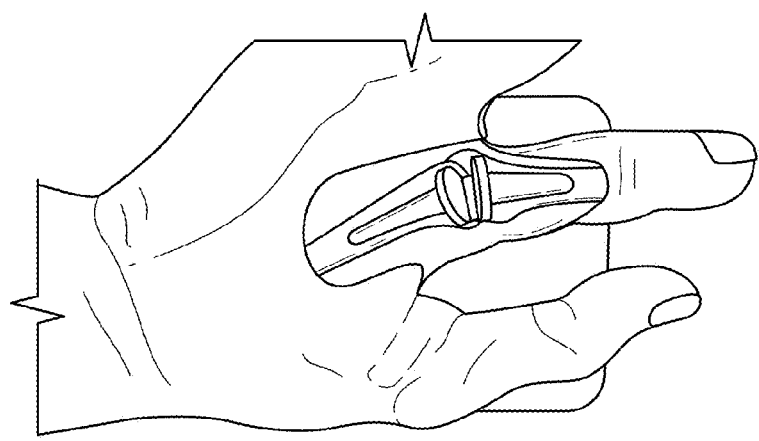
Figure 2C:
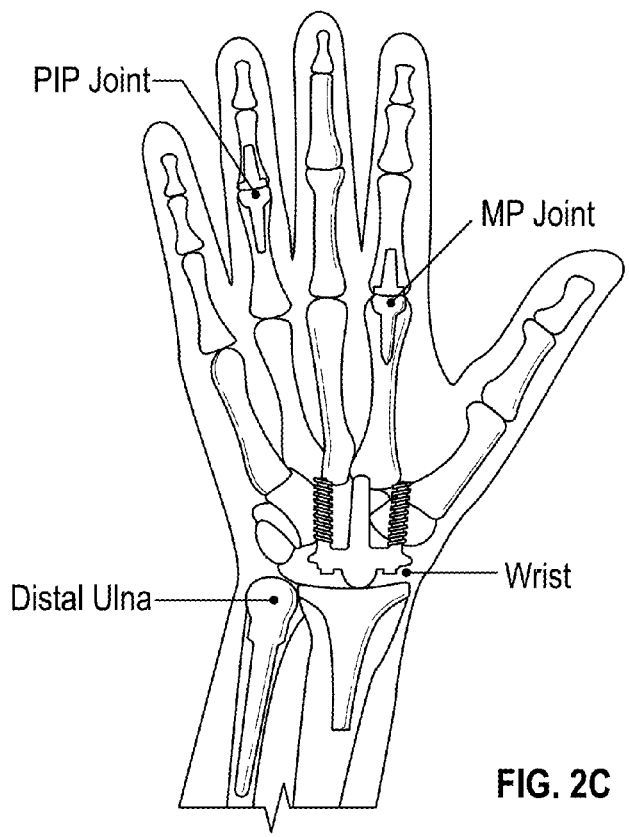
Figure 2D:
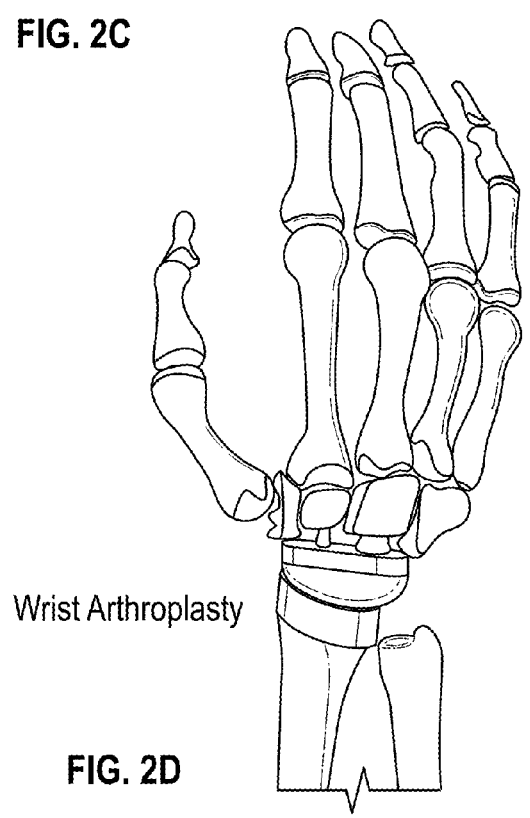
Figure 2E:
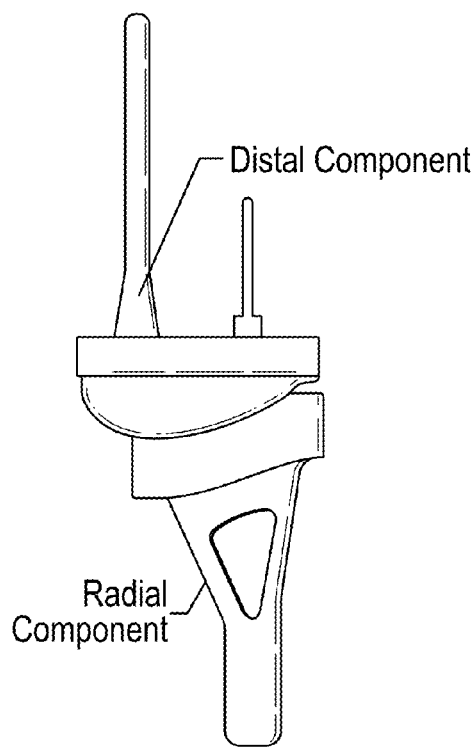
Figure 2F:
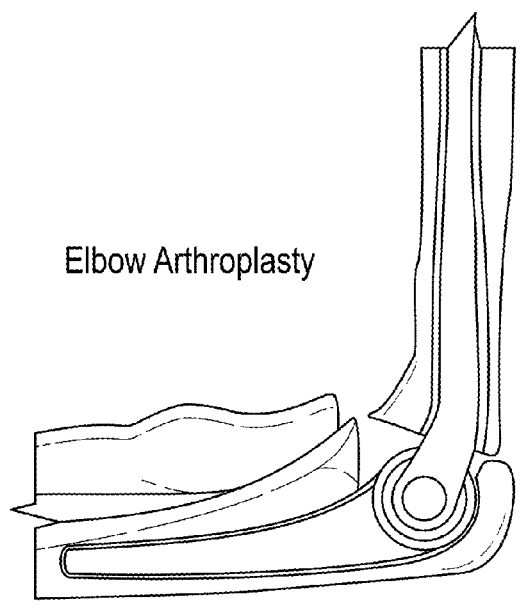
Figure 2G:
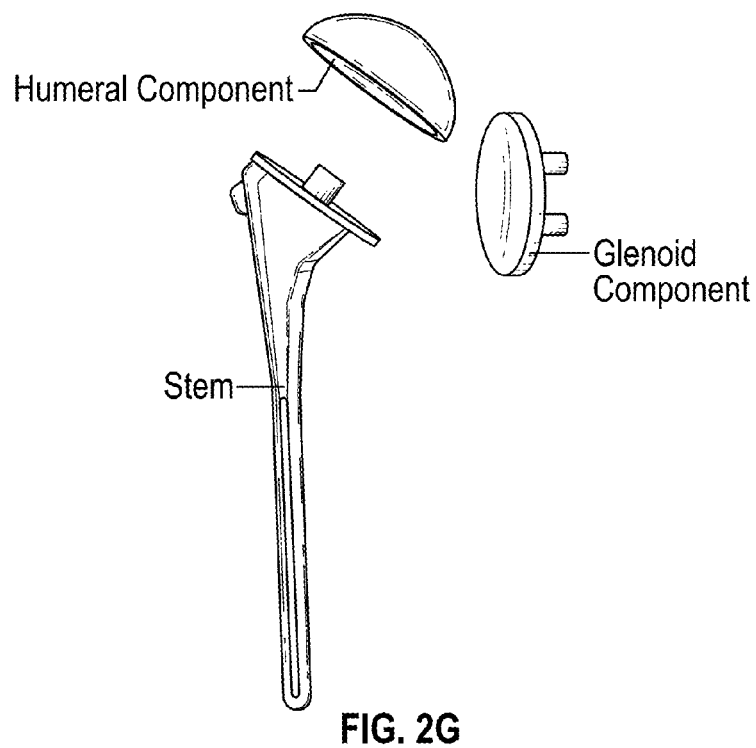
Figure 2H:
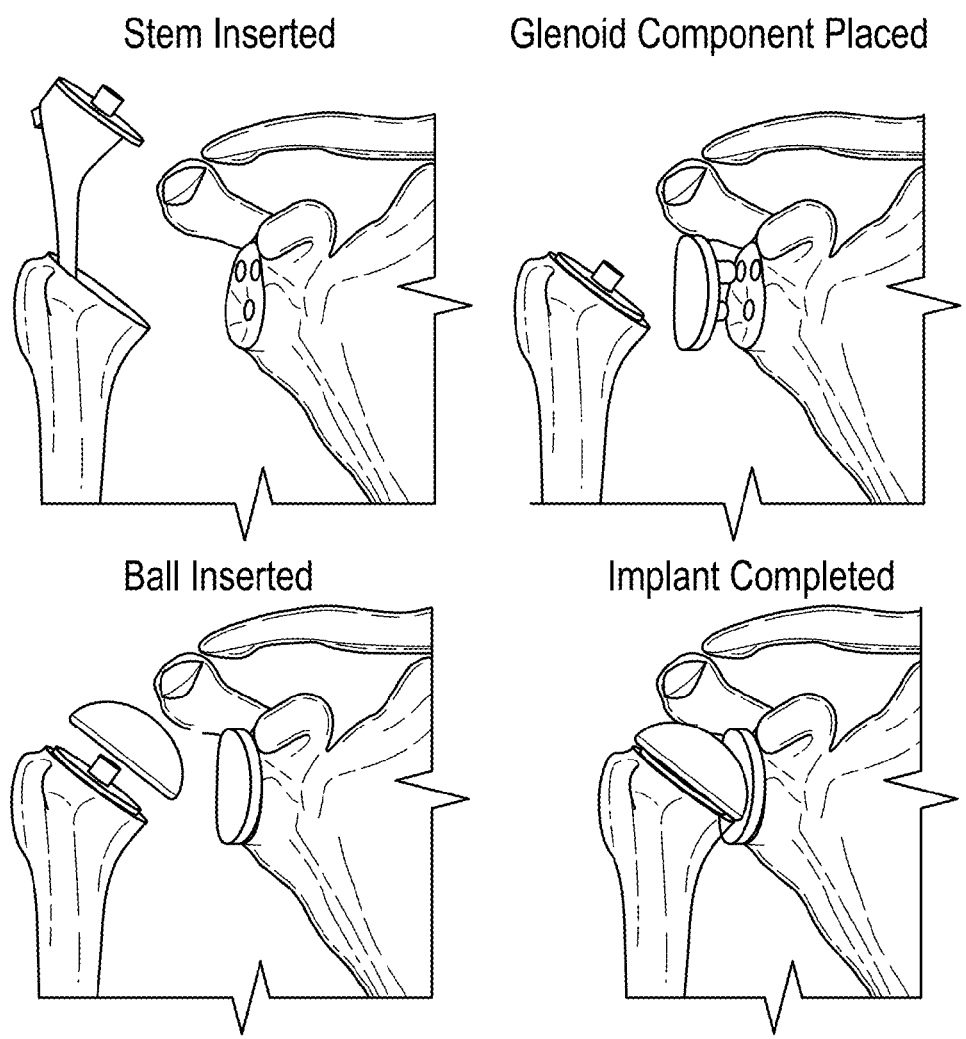
Figure 3A:
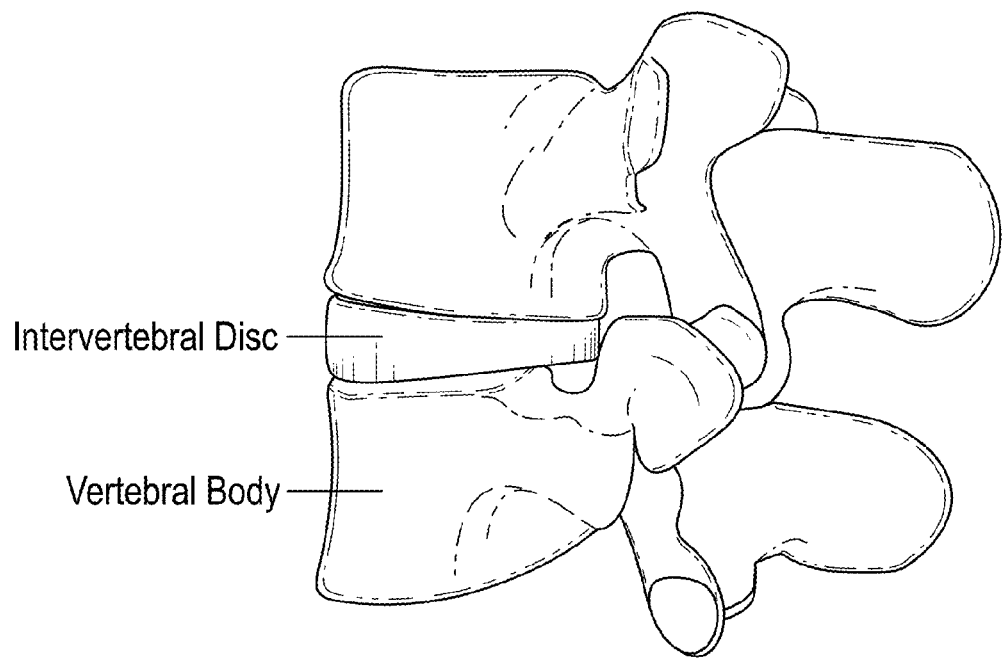
FIGS. 3A to 3F are illustrative representations of additional devices and applications that may incorporate the teachings of the present disclosure.
Figure 3B:
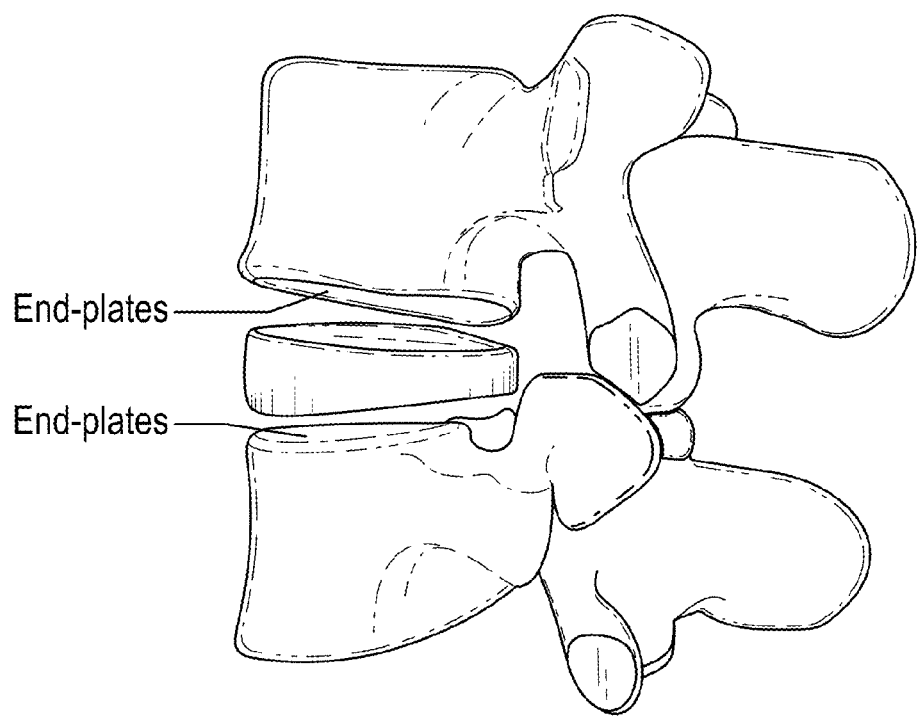
Figure 3C:
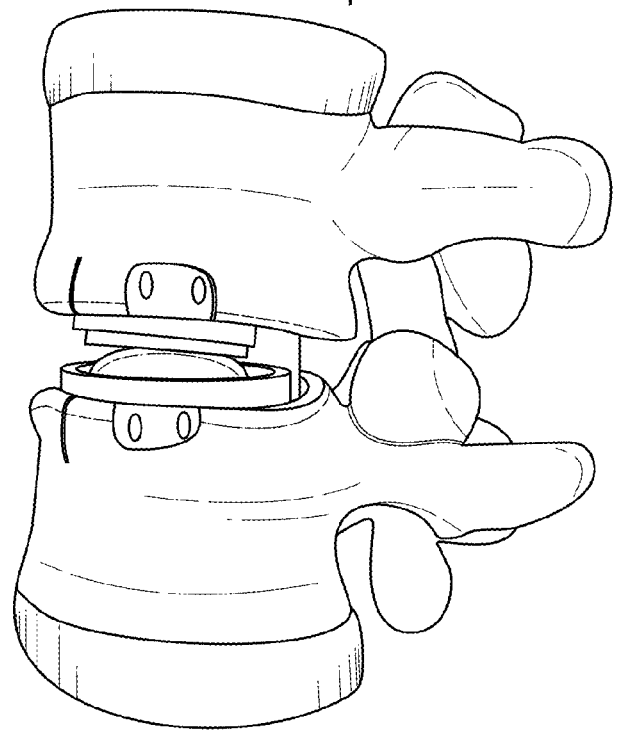
Figure 3D:
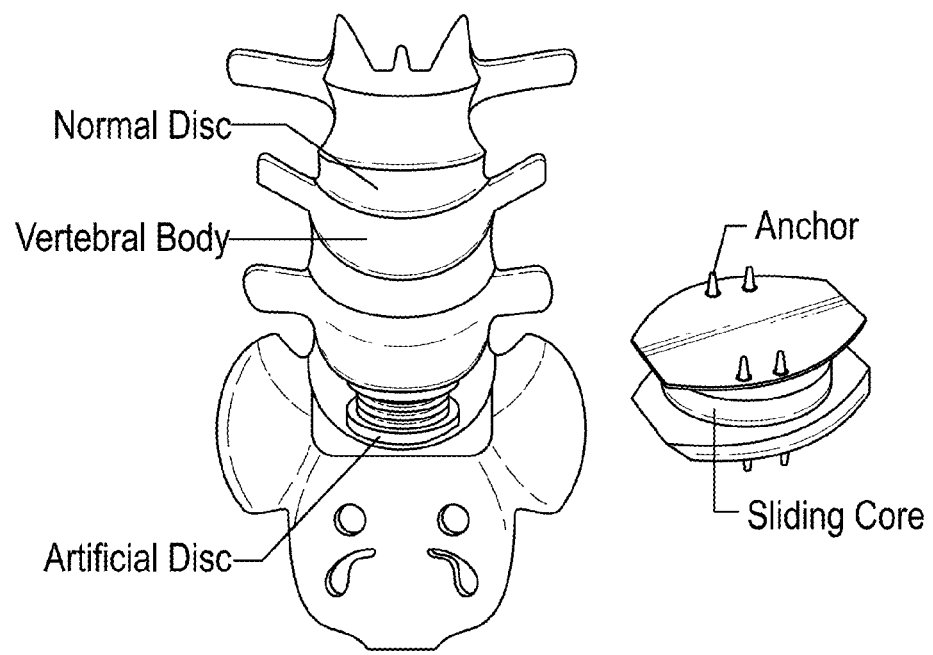
Figure 3E:
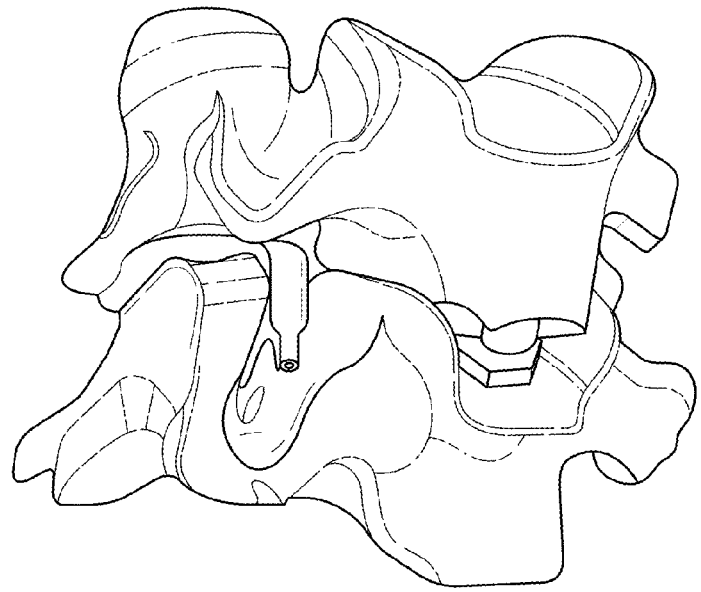
Figure 3F:
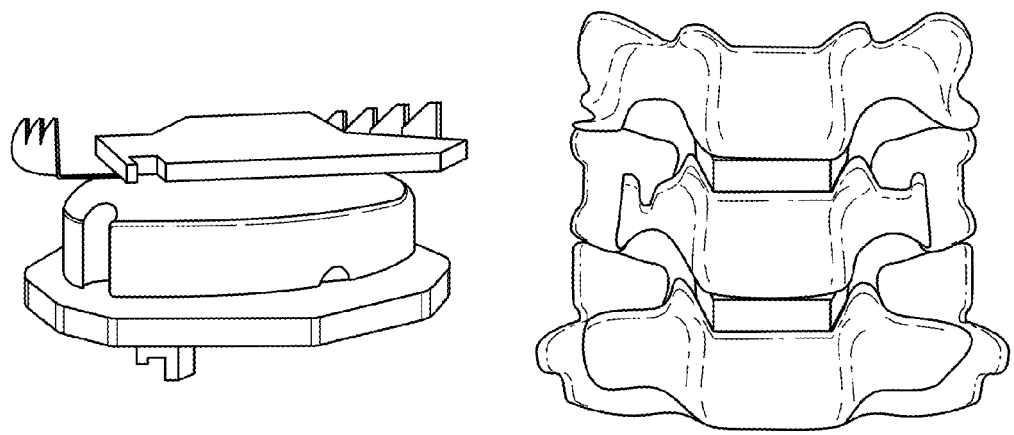

Thus, for example, in a hip replacement (e.g., FIGS. 1A and 1B) or any two opposing articular joint surfaces (e.g., knee replacement (e.g., FIGS. 1C-1E; FIGS. 11A-11C), shoulder replacement (e.g., FIGS. 2G-2H), spinal disc replacement (FIGS. 3A-3F) or any other joint replacement), it is possible to apply the disclosed thin film ternary ceramic coatings to opposing surfaces to provide protected articulable contact therebetween. This approach obviates the need for an opposing articular component (e.g., UHMWPE insert) assembled to the socket component (or glenoid), such that the socket component could be a single piece. Such a socket component could be thin enough to load bone more physiologically (thereby reducing bone density loss through stress shielding) and strong and supportive enough to endure loading for the span of its service life. However, the ceramic-coated titanium alloy component could also articulate against an opposing UHMWPE articular surfaces (e.g., a UHMWPE component in a monoblock construct as described below) without failure or deleterious effect. In addition, the disclosed thin film ternary ceramic coatings improve upon the tribological properties of current CoCr alloy-UHMWPE bearing couples. The articulating components of the disclosed joint replacement assembly result in a construct that can load adjacent supporting bone more physiologically (to retain or regain normal density), while minimizing or eliminating articulating wear and wear debris.

Although exemplary embodiments of the present disclosure contemplate fabrication of the components to be used in joint replacement and resurfacing from titanium alloy, it is further contemplated according to the present disclosure that such components may also be manufactured from one or more of a variety of materials, such as plastics, non-titanium metals (e.g., cobalt-chrome alloy), ceramics, etc. The outer surface of one or more of the components may be bonded to and/or coated with the disclosed thin film ternary ceramic coating (i.e., less than 20 micron thick layer) or ceramic-like coating (e.g., metal nitrides, carbides, oxides, or a combination thereof) to improve wear resistance (e.g., during articulation with the acetabular cup). The coating applied to the component may have tailored properties (e.g., hardness and/or surface properties) to reduce potential for wear and/or to reduce the coefficient of friction.

Thus, in exemplary implementations of the present disclosure, a bore of a femoral head may be bonded and/or coated with a thin film ceramic or ceramic-like coating (e.g., metal nitrides, carbides, oxides, or a combination thereof) to obviate fretting, crevice corrosion, galvanic reaction at the junction between the bore of the femoral head and the cooperative fitting of the stem. Further the femoral head could have a hollow interior for cost reduction, material conservation, weight, etc. For example, a titanium alloy femoral head could be 3D printed to include a hollow center.

Further, the component may be provided with a surface geometry (e.g., surface-machined pattern) of micro-grooves (e.g., spiral micro-grooves) or any other type of disrupted surface to maintain lubricity (e.g., entrap lubricating joint fluid) and decrease the coefficient of friction. The articulating surfaces of the device may be coated with the disclosed thin film ternary ceramic. Even more, ultra-small grain size thin film ceramic coatings may be achieved based on application modality, (e.g., application via cathodic arc vapor deposition), thereby resulting in a dense, highly integral, and firmly attached coating with high surface energy to reduce wear.

3. Thin Film Ternary Ceramic Coating:

The disclosed thin film ternary ceramic coatings may be applied to metal components as schematically depicted in the cross-sectional view of FIG. 10 (e.g., for use as modular junction fittings or articular surfaces) by chemical or physical vapor deposition, cathodic arc deposition, magnetron sputtering, and/or any other suitable technique. The disclosed coatings may be used on any joint replacement, resurfacing, or spine artificial disc device (or components thereof). In exemplary implementations of the present disclosure, a thin film ternary ceramic-coated metal component articulates against a similar thin film ternary ceramic-coating metal component. However, the present disclosure is not limited by or to systems wherein the same or similar coating materials are in opposing contact.

Exemplary thin film ternary ceramic coatings according to the present disclosure include titanium aluminum nitride (TiAlN), titanium carbon nitride (TiCN), titanium niobium nitride (TiNbN), titanium silicon nitride (TiSiN), titanium zirconium nitride (TiZrN), titanium chromium nitride (TiCrN), and the like. The disclosed thin film ternary ceramic coatings may be used in combination with titanium alloy coatings, ceramic-like material coatings (e.g., metal nitride, metal carbide, metal oxide, or a combination thereof), carbon-based diamond, carbonaceous material (e.g., diamond-like carbon (DLC)), or any of the class of metallic nitrides. The use of non-identical coating materials (e.g. one surface harder than its opposing articulating surface) for opposed surfaces may be advantageous to facilitate relative articulation therebetween.

Of note, the metal surface to which the disclosed thin film coating is applied may be textured (e.g., roughened surface, plasma sprayed, acid etched, porous coated, etc.) to better engage the femur (or other joint replacement device) and/or provided with a coating (e.g., to assist in healing, to better engage the bone, etc.). As noted above, the disclosed thin film ternary ceramic coating may be applied at thicknesses of less than 20 microns.

4. Isoelastic Implant Considerations:

Joint replacement or resurfacing devices are generally employed to replace arthritic or damaged joint anatomy. In so doing, there is a need to closely match the elastic modulus of the host bone/anatomy being replaced in order to avoid stress shielding to maintain the patient's bone density. The longevity and efficacy of the implant is in part dependent on the stability and strength of the underlying bone to which it is attached. Therefore, developing porous structured implants with variable modulus to better match the patient's anatomy is important to the long-term health of the patient and life of the implant.

Exemplary implementations of the present disclosure provide isoelastic joint replacement devices, systems and methods that may include a porous structure, as discussed below. The disclosed joint replacement device may be isoelastic or of an equivalent flexural stiffness relative to the supporting bone. The disclosed joint replacement device may include a multi-layered construct with a thin cross-section (e.g., thin layered sections), enabled by hardening the articulating surface of the device using a wear resistant coating. The multi-layered construct may further include a porous structure that approximates the stiffness of the host bone (e.g., more closely matches the native anatomy) to maintain healthy bone density and fixation of the device within the patient (e.g., to conserve denser and supportive bone adjacent to the original physiologic articular surface). This type of bone preservation, in combination with the isoelasticity of the device, allows for more physiologic loading of the bone and joint mechanics to be created for the device, and leaves behind more bone stock for implant support and for possible revisions of the primary joint replacement procedure.

Further, a joint replacement device may advantageously exhibit porosity that supports ingrowth. Use of titanium alloy as an articulating component substrate enables use of porous titanium constructs integral to the articular bearing surface, where the porosity thereof could be beneficial to bony ingrowth and implant attachment to the skeleton. According to exemplary implementations of the present disclosure, the ingrowth material/region comprising the surfaces of the device may also coated with a ceramic or other synthetic compound to attract and maintain bone for fixation.

Figure 4:
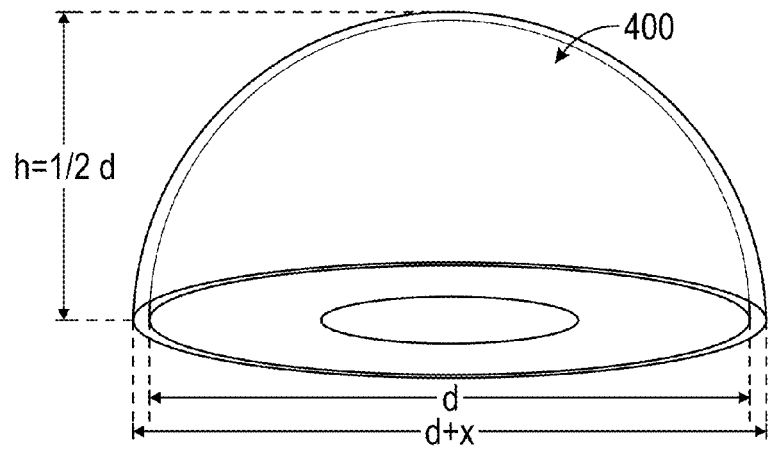
FIG. 4 is a schematic view of an exemplary acetabular cup.

With reference to FIGS. 4-7, advantageous aspects of the present disclosure are described with reference to an exemplary acetabular cup. FIG. 4 provides a hemi-elliptical acetabular cup or hemi-elliptical shell 400 that may be beneficially employed in hip implant applications. The shape of the hemi-elliptical cup could have a major elliptical diameter across the opening (e.g., mouth) of the cup where a theoretical ellipse would be halved to form a hemi-ellipse, and a minor diameter of the ellipse at a polar axis of the cup (e.g., the apex of which is implanted furthest into the acetabulum of a patient). Accordingly, the opening of the cup is substantially circular, but the profile of the cup is substantially hemi-elliptical. More specifically, the opening of the hemi-elliptical cup with a particular depth (e.g., height) is larger than the opening of a hemi-spherical cup with the same depth (e.g., height). A hemi-elliptical cup could facilitate insertion of the cup into a patient because the reaming tool used to prepare a joint (e.g., hip) to receive the cup is usually hemi-spherical. Accordingly, a surgeon could use a larger sized reaming tool as the depth of the hemi-elliptical cup is the same as a hemi-spherical cup, but the opening (e.g., mouth) of the hemi-elliptical cup is wider, thereby providing a tighter fit in the patient (e.g., pushes into bone better).

Figure 5A:
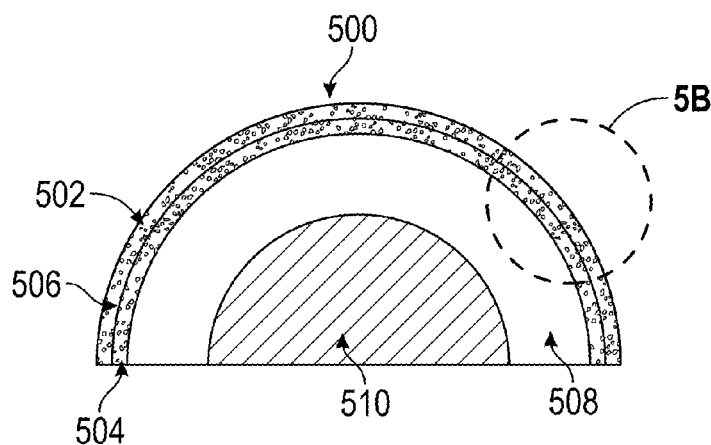
FIGS. 5A-5B are cross-sectional views of exemplary acetabular devices with coatings applied thereto.
Figure 5B:
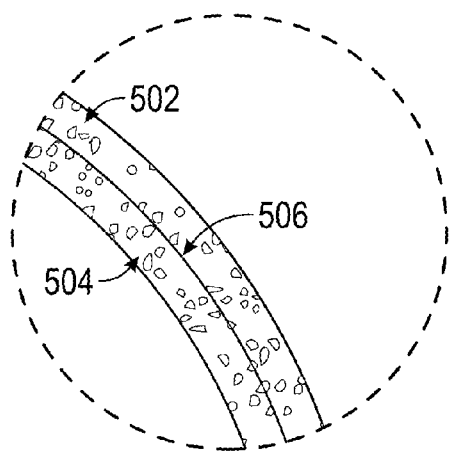

FIGS. 5A and 5B are cross-sectional views of an exemplary coated acetabular cup 500 according to an exemplary embodiment of the present disclosure. The coating techniques disclosed with reference to FIGS. 5A and 5B could be used for various devices (e.g., partial or total hip replacement, hip resurfacing, etc.), knee replacement (e.g., partial or total knee replacement), shoulder replacement (e.g., glenoid component thereof), ankle replacement (e.g., talus component thereof), spinal disc replacement, etc.

The disclosed porous coated device could comprise a metal cup (e.g., a thin ultra-porous structured metal acetabular cup) with a bearing material (e.g., UHMWPE liner, embedded material, etc.) molded or embedded at a surface and into an inner region thereof. The cup could comprise a barrier wall (e.g., substantially thin solid metal wall, etc.) defining a hemisphere at a predefined depth relative to the surface of the cup. Thus, as shown in the cross-sections of FIGS. 5A and 5B, an outer porous region 502 is separated from an inner porous region 504 by a barrier wall 506. The term "barrier wall" is used broadly to encompass a structural feature within the cup (or other device) that serves to block or inhibit flow of a bearing material, (e.g., a bearing material that is molded or embedded relative to a surface of the cup). Thus, the barrier wall 506 may take the form of a reduced porosity region or plane (e.g., an arcuate plane) defined within the cup. The cup and the associated barrier wall may be advantageously fabricated from a corrosion-resistant material (e.g., titanium/titanium alloy) using a laser sintering process, a diffusion bonding process, a vapor deposition process, etc. The overall stiffness of the construct can more closely approximate the normal load transfer of stress to the surrounding host bone.

The cup 500 or other joint device may also include an outer porous layer 502 that advantageously functions to encourage bony ingrowth to enhance security of the disclosed device (e.g., acetabular cup) to a patient. In exemplary embodiments, the porosity of the component may be optimized for bony ingrowth. The outer porous layer could be approximately 0.1 mm to 5 mm thick, and could exhibit a porosity of about 40% to 80% by volume. The barrier wall 506 (between the inner interrupted surface and the outer porous layer) could be of any suitable metal or metal alloy (e.g., titanium alloy) and of any thickness that will accommodate an isoelastic structure. Further, the barrier wall 506 may advantageously provide enhanced structural rigidity for impaction and implantation thereof. The cup 500 may include a monoblock construction, e.g., through introduction of a polyethylene (e.g., UHMWPE) inner layer 508 that is secured/embedded with respect to the inner porous layer 504 and that defines a bearing surface for articulation relative to a corresponding head 510. Thus, the disclosed implant may include porosity melding into a thin solid layer and then again into a porous construct that defines incorporates HWMPE on one surface, but facilitates and supports bone ingrowth on the other porous surface.

Further, the cup 500 could include a solid metal ring integrally or separately attached at the opening (e.g., mouth) thereof. The solid metal ring may serve to increases hoop strength (e.g., prevents collapse of the opening) and also facilitates surgical insertion into a patient (e.g., provides an impact surface for a surgeon to exert force upon without damage to the structural integrity of the cup).

Figure 6:
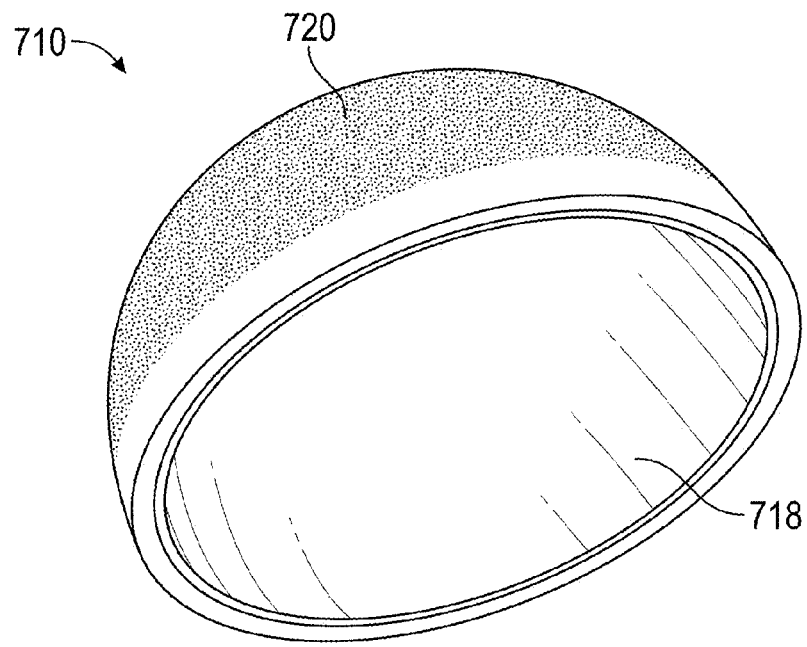
FIG. 6 is a perspective view of an exemplary acetabular component of a joint replacement device according to the present disclosure.
Figure 7:
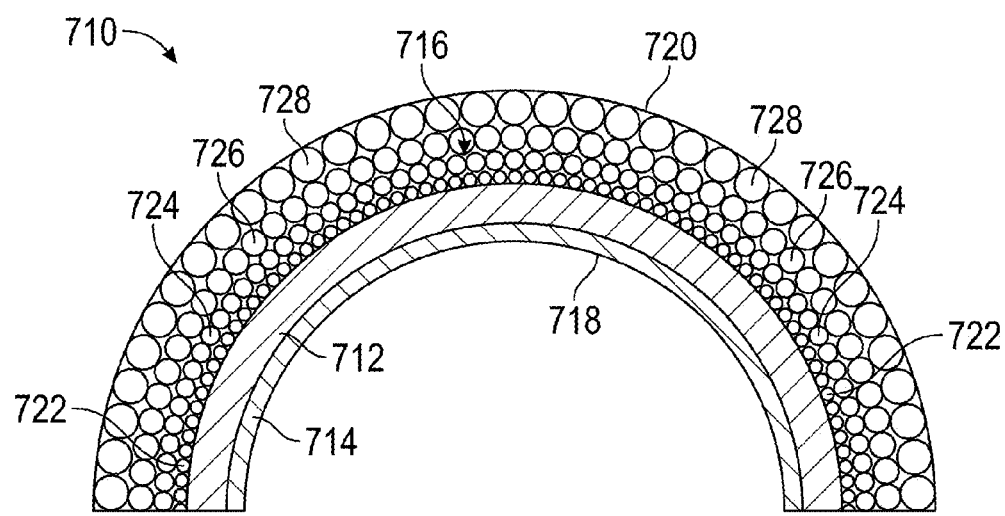
FIG. 7 is a cross-sectional side view of the exemplary acetabular component of FIG. 6.

FIGS. 6-7 are views of an exemplary acetabular component 710 (e.g., acetabular cup, acetabular shell, etc.) of an isoelastic joint replacement device (e.g., joint reconstruction device, prosthetic construct, implant design, etc.). More specifically, FIG. 6 is a perspective view of an isoelastic acetabular component 710 of a hip replacement device. The acetabular component 710 is isoelastic to bone which preserves bone stock in the native acetabulum when implanted in a patient. As shown, the acetabular component 710 is generally hemispherical in shape to receive a femoral head of a femoral implant (described in more detail below). Further, the acetabular component 710 permits the use of a large femoral head size, which provides the patient a more desirable anatomic range of motion with respect to the possibility of joint dislocation, thereby reducing the risk of post-operative hip joint dislocation.

FIG. 7 is a cross-sectional side view of the acetabular component 710 of FIG. 6. As shown, the acetabular component 710 is a multi-layered construct of several layers, all formed in a generally hemispherical shape adjacent to one another. More specifically, the acetabular component 710 includes an articulating layer 714, a variably porous layer 716, and a metal substrate layer therebetween 712.

The metal substrate layer 712 is the middle layer between the articulating layer 714 and the porous layer 716. More specifically, the metal substrate layer 712 is a thin solid metal substrate (e.g., cobalt chromium, titanium alloy, stainless steel, etc.), and could be up to a thickness that will not, by itself negate the isoelastic properties of the device.

Attached to (e.g., coated onto) the inner surface (e.g., concave surface) of the metal substrate layer 712 is an articulating layer 714. The articulating layer 714 is the innermost layer (e.g., the layer closest to the center of the hemispherical shape) and defines an interior articulating surface 718 (e.g., articular surface), which directly contacts and interacts with a femoral head of a femoral implant (described in more detail below). The articulating layer 714 may be approximately 1 to 20 microns thick and may include a hardening and wear resistant thin film coating to harden the interior articulating surface 718 of the acetabular component 710, thereby increasing durability and corrosion resistance, and obviating metal debris and metallic ion release. For example, the wear resistant coating could be a thin film ternary ceramic coating as described herein, including but not limited to titanium aluminum nitride (TiAlN), titanium niobium nitride (TiNbN), titanium silicon nitride (TiSiN), titanium zirconium nitride (TiZrN), titanium chromium nitride (TiCrN), or another coating such as diamond-like carbon (DLC).

Adjoined to the outer surface (e.g., convex surface) of the metal substrate layer 712 is porous layer 716. The porous layer 716 may be approximately 0.5 to 5 mm thick and composed of the same material as the solid metal substrate layer 712. The porous layer 716 is the outermost layer (e.g., the layer farthest from the center of the hemispherical shape) and defines an exterior anchoring surface 720. The porous layer 716 is intended to be adjacent to host bone in situ, such that the exterior anchoring surface 720 directly contacts and is fixed to a bony socket of a patient. Further, the interior articulating surface 718 is opposite the exterior anchoring 720 surface of the joint replacement device, thereby resurfacing both articulating sides of the joint to be replaced.

The porous layer 716 advantageously exhibits a porosity to more closely approximate the stiffness of the host bone, so that the bone is more physiologically loaded to maintain healthy bone density and fixation of the device (e.g., prevent stress shielding). The joint replacement device (e.g., implant) may include a multi-layered construct that incorporates an ultra porous structured (UPS) bone apposition surface which seamlessly blends into a solid metal substrate that is surface coated with a coating disclosed herein, e.g., a thin film ternary ceramic or thin film diamond-like carbon (DLC).

For example, as shown in FIG. 7, there are four bands within the porous layer 716. The first band 722 is adjacent to the metal substrate layer 712 and is the least porous (greatest density). In this way, the first band 722 could provide a seamless blend (e.g., seamless connection, seamless transformation, etc.) from the porous layer 716 to the solid metal substrate layer 712. The second band 724 from the metal substrate layer 712 is more porous (greater density) than the first band 722. The third band 726 from the metal substrate layer 712 is more porous (greater density) than the second band 724 and the first band 722.

The fourth band 728 from the metal substrate layer 712 is the most porous (greatest density). The fourth band 728, being the most porous, is where the porous layer 712 (and the entire articular component 710) is most flexible. This porosity at the exterior of the acetabular component 710 could encourage bone ingrowth therewith. Further, the fourth band 728 (and the exterior anchoring surface 720) could be textured such that the texture and increased surface area facilitates attachment (e.g., cement-less bony attachment) to a bony socket (e.g., reamed bony socket) of a patient. Although the variable density of the acetabular component 710 is described to be in bands or layers, the porosity could alternatively have a more gradual transition from greater porosity to lesser porosity, wherein the changing density is blended rather than banded.

The articular component 710 shows a single porous layer 716 with porosity that gradually increases from an interior surface to an exterior surface thereof. However, one or more porous layers could be used, and other porosity configurations could be implemented. For example, there could be two layers of porosity separated by an additional thin metal layer, the porosity could be configured (e.g., patterned) such that porosity gradually increases from the apex of the hemisphere to the base of the hemisphere, the porosity could be configured in abrupt layers (instead of gradual), and/or the porosity could be configured randomly. The porosity may also be uniformly structured using an average pore size ranging between 200 microns and 600 microns.

The component to which the disclosed coating is applied could include one or more materials for purposes of wear resistance, strength, durability, weight, etc. The outer surface of the component could comprise a 3D porous material, such as for attachment (e.g., cement-less bony attachment) to a bony socket (e.g., reamed bony socket) of a patient. The composition of the cross-section of the component could gradually (or abruptly) change from a 3D porous material at the outer surface to a titanium alloy at the inner surface.

The 3D porous material could include a coating (e.g., thin film ternary ceramic (e.g., TiAlN), phosphate (e.g. $CaPO_4$, HA, bisphosphonates), and/or other synthetic compound (e.g. biodegradeable polymer)) to attract and/or maintain bone attachment of the device. Further, the inner surface of the component could include a thin film ceramic coating to prevent wear and debris. The ability to achieve isoelasticity is a function of the modulus of the materials used in the replacement as well as the sectional size/properties of those materials within the overall construct. Using a thin film articulating ceramic, the monolithic nature of the component on either side of the joint can be minimized. This yields benefits of improved load transfer and reduced bone resections, especially in joints where bone stock for fixation is limited, such as in shoulders, ankles, digits, and upper extremities.

Of note, the term "modulus" technically refers to a property of a material, not the flexibility/properties of a construct. For example, titanium alloy has a modulus of 115 mPa and bone has a modulus of about 15 mPa. According to the present disclosure, the unique and advantageous construct—which combines the underlying material properties, porosity parameters, coating properties and dimensional characteristics (e.g., relatively thin construct)—beneficially provides an implant that closely approximates the modulus of the host bone, thereby providing isoelasticity and avoiding potential stress shielding. More particularly, the overall constructs/implants disclosed herein are effective in translating a relatively "stiff" material, e.g., a titanium alloy with a modulus of 115 mPa, to a relatively "flexible" construct exhibiting an overall modulus that is essentially equivalent to the construct of bone that supports it.

Various joint resurfacing and replacement devices (and/or components thereof) may be fabricated and used according to the teachings of the present disclosure. For example, hip replacement devices, knee replacement devices (e.g., for total knee replacement, partial knee replacement), and foot prosthetic devices (e.g., ankle prosthetic devices) may be implemented. Further, finger implant devices, wrist implant devices, elbow arthroplasty devices, and shoulder replacement devices may be implemented. Still further, lumbar disc replacement devices and cervical disc replacement devices (e.g., open or closed wedges) may be implemented. These devices are only exemplary, and the coatings described above (and/or any other teaching discussed herein) could be applied to any joint in the body.

Any thin film coating discussed herein could be applied to a modular junction, an articulating surface, and/or a joint device (and/or components thereof) that is fused to the bone of a patient (e.g., the joint device may articulate against a bone, cartilage, or other articulating geometry of a joint, or against another prosthetic component).

Figure 8:
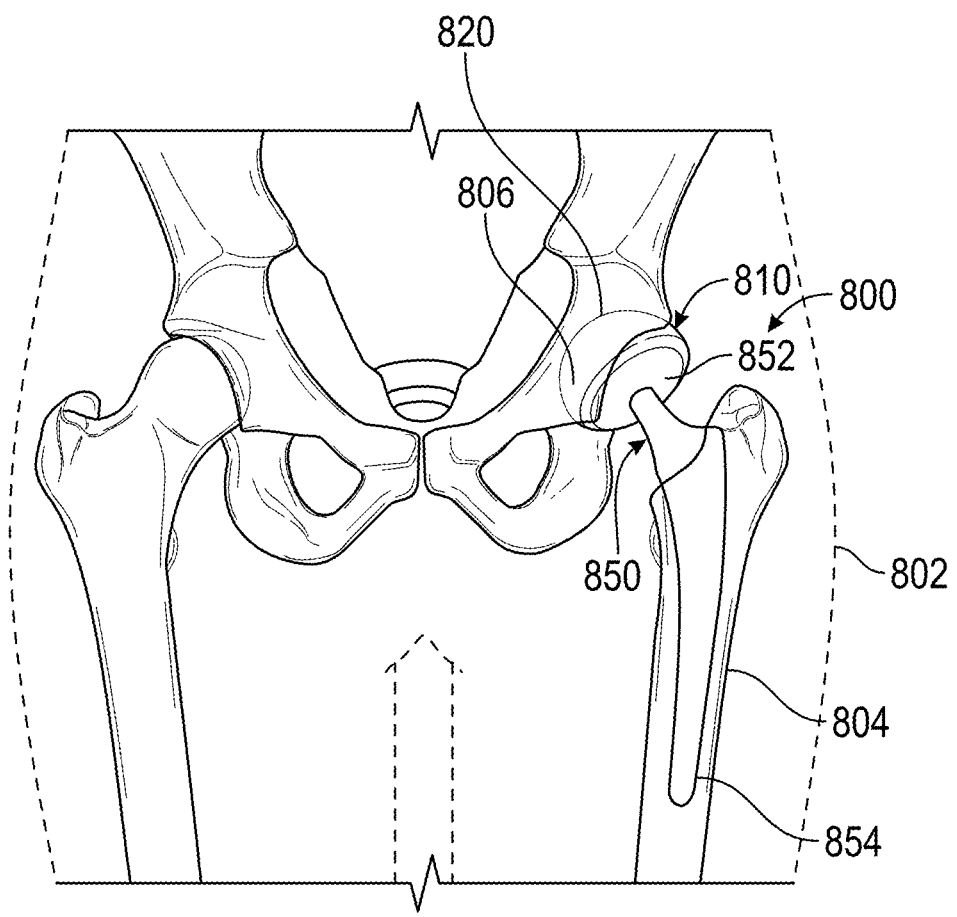
FIG. 8 is a view of a joint replacement device, including the exemplary acetabular component of FIGS. 6 and 7, surgically implanted in a patient.

FIG. 8 is a view of a joint replacement device 800 surgically implanted into a patient 802. The isoelastic joint replacement device 810 affixes and articulates on both sides of a joint replacement. The joint placement device 800 includes an acetabular component 810 (as described above) and a femoral implant 850 (e.g., mating component). The femoral implant 850 includes a prosthetic femoral head 852 and a hip stem 854. The hip stem 854 is a conventional hip stem, and as such, is not isoelastic. It can be, however, coated with a thin-film ternary ceramic to improve its bone affinity and to protect host tissues from metal ion release.

The acetabular component 810 is surgically attached to the bony socket 806 of the patient 802. More specifically, the outer anchoring surface 820 of the acetabular component 810 is surgically attached (e.g., cement-less bony attachment) to a bony socket 806 (e.g., reamed bony socket) of the patient 820. Flexibility of the acetabular component 810 (from porosity, density, and/or a thin cross-section) at or near the level of the flexibility of the bone itself avoids stress-shielding (and any associated decreased supporting bone density), which could contribute to loosening of the joint replacement device 800 from the host bone. Isoelasticity of the acetabular component 810 can be varied by altering the porosity, density, and/or thickness of the porous layer of the acetabular component 810, and/or by altering the density and/or thickness of the metal substrate layer of the acetabular component 810.

The femoral head 852 mates with the acetabular component 810 to provide articulation (e.g., relative motion) therebetween. Articulation between an outer surface of the femoral head 852 of the femoral implant 850 and the inner surface of the acetabular component 810 provides articulation of the femur 804 relative to the hip center. The composition of the alloying materials (e.g., diamond-like carbon (DLC), ceramic (e.g., thin film ternary ceramic such as titanium aluminum nitride (TiAlN), titanium niobium nitride (TiNbN), titanium silicon nitride (TiSiN), titanium zirconium nitride (TiZrN), or titanium chromium nitride (TiCrN)), titanium nitride, zirconia alumina) of the articulating layer of the acetabular component 810 could differ from that of the femoral head 852 in hardness to optimize the coefficient of friction, enhance lubricity, and/or decrease potential wear at the articulating surface. Further, the femoral head 852 could have a titanium head with a thin film ternary ceramic surface coating articulating against ultra-high-molecular weight polyethylene (UHMWPE) of the acetabular component 800.

Functionalization of the thin film coating may be advantageously effected to achieve desired levels of hydrophilicity, e.g., based on autoclave conditions (temperature/moisture), chemical treatment and the like. In this way, desired levels of bone growth may be promoted/achieved according to the present disclosure. Moreover, improved or enhanced hydrophilicity advantageously increases lubricity, improves articular wear properties and provides the potential for improving the biologic environment to accommodate osteoblast proliferation and adhesion.

Figure 9:
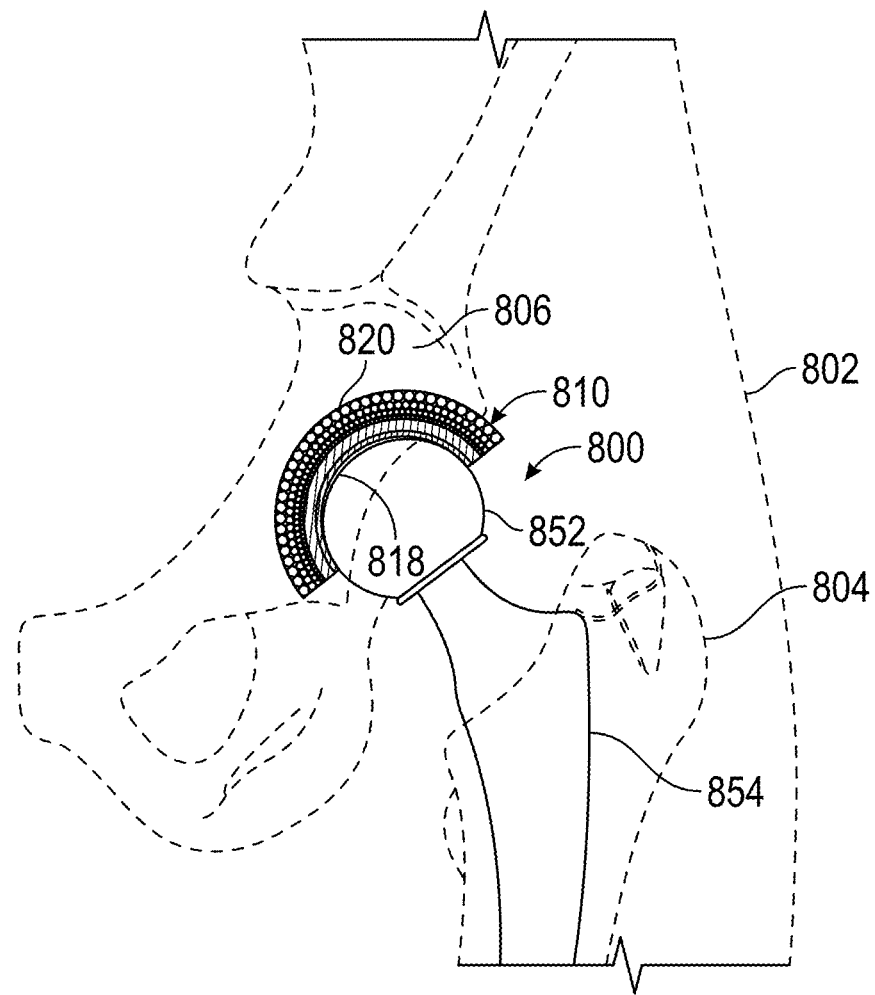
FIG. 9 is a view of the implanted joint replacement device of FIG. 8 with the exemplary acetabular cup shown in cross-section.

FIG. 9 is a view of the implanted joint replacement device 800 of FIG. 8 with the acetabular component 810 shown in cross-section. The porosity (e.g., flexural stiffness) of the acetabular component 810 varies in cross-section so as to more closely match that of the host bone. The design and architecture of the acetabular component 810 encompasses a thin cross-section that necessitates and incorporates a bearing surface on both sides of the joint. The porosity of the exterior anchoring surface 820 (e.g., bone ingrowth side) of the acetabular component 810 is engineered to better accommodate its use in various orthopedic applications.

Although the joint replacement device 800 has been described in association with a hip replacement device, the above disclosure could be used with a variety of other prosthetic devices (e.g., knee, shoulder, ankle, spinal disc, other joints, etc.) as further described in FIGS. 1A-1G, FIGS. 2A-2H, FIGS. 3A-3F and FIGS. 11A-11C. As described herein, articulating wear resistance is enhanced via the thin film ternary ceramic coating while maintaining the isoelasticity of the joint replacement or resurfacing design. Wear may be further precluded by enhanced geometrical design of cooperating elements, articular surface modification, super-polishing, and/or optimization of ceramic coating grain size.

Having thus described the constructs, designs, materials and methods of use and manufacture of articulating devices, as well as protection of metallic junctions and fittings thereof, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

The invention claimed is:

1. A modular junction for an orthopedic application, comprising:
    a first metallic element defining a first portion;
    a second metallic element defining a second portion configured and dimensioned to receive at least a portion of the first portion;
    a thin film, non-porous ternary ceramic coating applied to at least one of the first portion and the second portion;
    wherein the thin film, non-porous ternary ceramic coating is selected from the group consisting of titanium aluminum nitride (TiAlN), titanium carbon nitride (TiCN), titanium niobium nitride (TiNbN), titanium silicon nitride (TiSiN), titanium zirconium nitride (TiZrN), titanium chromium nitride (TiCrN), and combinations thereof; and
    wherein the thin film, non-porous ternary ceramic coating is effective to prevent wear, fretting, metal ion release, and galvanic and crevice corrosion at the coated surface.

2. The modular junction of claim 1, wherein the thin film, non-porous ternary ceramic coating is functionalized to provide at least one of (i) improved wear properties, (ii) improved biological affinity of an implant that includes the first element and the second element, (iii) improved biological fixation of an implant that includes the first element and the second element, and (iv) to promote osteoblast activity for bone fixation of an implant that includes the first element and the second element.

3. The modular junction of claim 1, wherein the first and second metallic portions are configured and dimensioned as part of a hip implant or a knee implant.

4. The modular junction of claim 1, wherein the first element and the second element are configured and dimensioned for use in a joint replacement or joint resurfacing application.

5. The modular junction of claim 1, wherein the second element further comprises a polyethylene liner, insert or spacer.

6. The modular junction of claim 1, further comprising one or more intermediate coating layers between (i) at least one of the first element and the second element, and (ii) the thin film, non-porous ternary ceramic coating.

7. The modular junction of claim 1, wherein at least one of the first metallic material and the second metallic material is a cobalt chrome alloy.

8. The modular junction of claim 1, wherein at least one of the first metallic material and the second metallic material is selected from the group consisting of titanium, a titanium alloy and stainless steel.

9. The modular junction of claim 1, wherein the first metallic material and the second metallic material are the same metallic material.

10. The modular junction of claim 1, wherein the first metallic material and the second metallic material are different metallic materials.

11. The modular junction of claim 10, wherein one of the first metallic material and the second metallic material is a cobalt chrome alloy, and the other of the first metallic material and the second metallic material is titanium, a titanium alloy or stainless steel.

12. The modular junction of claim 1, wherein the thin film, non-porous ternary ceramic is applied at a thickness of 20 microns or less.

13. The modular junction of claim 1, wherein the first portion is a stem portion.

14. The modular junction of claim 1, wherein the second portion is a bore.

15. The modular junction of claim 14, wherein the bore is a tapered bore.

* * * * *

UNITED STATES PATENT AND TRADEMARK OFFICE
CERTIFICATE OF CORRECTION

PATENT NO. : 10,272,177 B2  
APPLICATION NO. : 15/638930  
DATED : April 30, 2019  
INVENTOR(S) : Alex Khowaylo et al.

Page 1 of 1

It is certified that error appears in the above-identified patent and that said Letters Patent is hereby corrected as shown below:

On the Title Page

Item (72) Inventors:  
Insert: --Douglas E. Wolfe, St. Marys, PA (US)--

Signed and Sealed this  
Twenty-fourth Day of September, 2019

Andrei Iancu  
*Director of the United States Patent and Trademark Office*